United States Patent [19]

Roberge et al.

[11] Patent Number: 4,991,093
[45] Date of Patent: Feb. 5, 1991

[54] METHOD FOR PRODUCING TOMOGRAPHIC IMAGES USING DIRECT FOURIER INVERSION

[75] Inventors: Wayne Roberge, Hopewell; Brian Flannery, Clinton, both of N.J.

[73] Assignee: Exxon Research and Engineering Company, Florham Park, N.J.

[21] Appl. No.: 390,936

[22] Filed: Aug. 8, 1989

Related U.S. Application Data

[63] Continuation of Ser. No. 160,011, Feb. 22, 1988, abandoned, which is a continuation of Ser. No. 767,902, Aug. 21, 1985, abandoned.

[51] Int. Cl.$^5$ .............................................. G06F 15/42
[52] U.S. Cl. .............................. 364/413.15; 364/413.2
[58] Field of Search ............................ 378/901, 21, 4; 364/413.13, 413.14, 413.15, 413.18, 413.19, 413.2

[56] References Cited

PUBLICATIONS

Robert M. Lewitt, "Reconstruction Algorithms: Transform Method", 1983, pp. 390–402.
Henry Stark, "Direct Fourier Reconstruction in Computer Tomography", 1981, pp. 232–244.

*Primary Examiner*—Jerry Smith
*Assistant Examiner*—Kim Thanh Tbui
*Attorney, Agent, or Firm*—Ronald D. Hantman

[57] ABSTRACT

The present invention is a method for examining at least a portion of an object using penetration radiation. The method includes the steps of transmitting radiation from an external source through the object in a plurality of coplanar rays, detecting the attenuated transmitted radiation after it has passed through the object, determining the projection data for said rays, and inverting said projection data to generate the distribution of the attenuation coefficient, wherein said inverting step includes the Direct Fourier Inversion Method such that the projection data is padded and the Fourier coefficients are filtered.

7 Claims, 19 Drawing Sheets

DFI + Pad + Filter distance from (x1,y1)

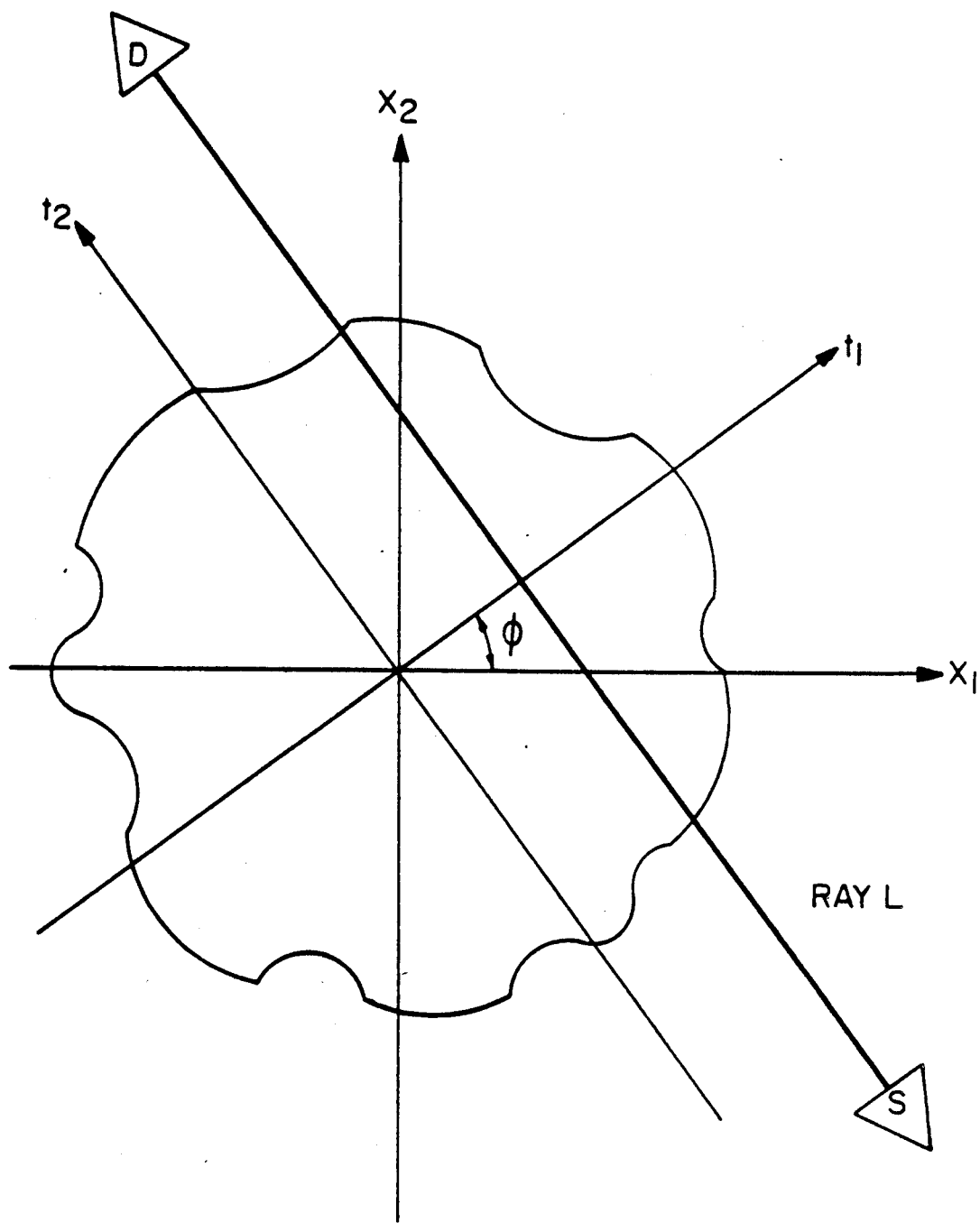
F I G. 1

TARGET

DFI

DFI + Pad

DFI + Filter

DFI + Pad + Filter

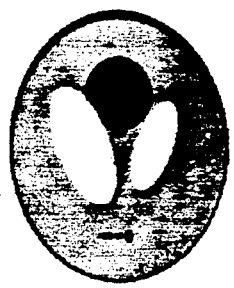
TARGET
FIG. 8
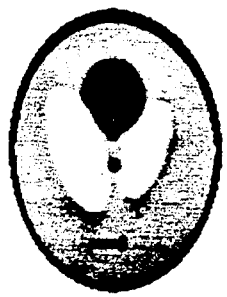
FBP
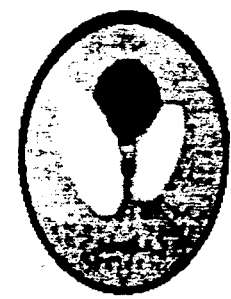
DFI

TARGET

FBP distance from (x1,y1)

DFi + Pad + Filter

METHOD FOR PRODUCING TOMOGRAPHIC IMAGES USING DIRECT FOURIER INVERSION

CROSS REFERENCE TO RELATED APPLICATIONS

This application is a Rule 60 continuation of U.S. Ser. No. 160,011 filed Feb. 22, 1988, which was a Rule 60 continuation of U.S. Ser. No. 767,902 filed Aug. 21, 1985, both now abandoned.

BACKGROUND OF THE INVENTION

The present invention relates to tomography, that area of technology which obtains an image of internal parts of an object in a plane through the object. In particular, the present invention relates to computerized tomography.

Computerized tomography (CT) refers to the procedures used to generate two dimensional maps of some physical quantity in a planar section of a target by measuring and analyzing the attenuation of beams of penetrating radiation passed through the target along sets of coplanar rays. As practiced, a complete apparatus must contain four elements: (1) a source of penetrating radiation, (2) detectors that measure the transmitted intensity of the radiation after passage through the target, and that can be calibrated also to give the unattenuated intensity of radiation in the absence of the target, (3) a computational device to store and process the attenuation measurements, converting them into a digital map of attenuation coefficients in the observed plane of the target, and (4) a device to display the resultant image.

Computerized tomography can be practiced in many ways, but the broadest commercial usage is in medical radiology to provide diagnostic maps of bone and tissue structure in human patients (see, Swindell, W. and H. H. Barrett, 1977, "Computerized Tomography: Taking Sectional X-Rays", Physics Today, pp. 32–41; Jaffe, C. C., 1982, "Medical Imaging", American Scientist, vol. 70, pp. 576–585; and Alexander, P., 1983, "Array Processors in Medical Imaging", Computer, vol. 16, pp. 17–30). Medical CT uses broad band bremsstrahlung X-ray tubes to produce penetrating radiation that is measured, typically, by scintillation crystals and phototubes. Measurements are stored in a programmable digital computer and analyzed using a method generically referred to as filtered (or convolution) backprojection (referred to hereafter as FBP). The density map derived from the analysis is displayed on a cathode ray tube as a two dimensional image containing perhaps 250×250 or 500×500 elements or pixels, with a resolution of about 1 millimeter, and 1% accuracy in determination of X-ray attenuation coefficient. However, special purpose tomography probes have been built using other types of radiation and detectors, such as gamma rays, and ultrasound.

The present method has applications to commercial medical CT and, in general, to any tomographic analysis, especially those where the image format contains large numbers of pixels. At present there is great interest across many industries to develop tomographic testing devices. In fact, the ability to handle routinely large format images could stimulate development of a new class of nondestructive testing apparatus based on tomography.

Several manufacturers including Picker, GE and EMI, produce medical CT scanners that are installed in thousands of hospitals throughout the US and world, at costs ranging from a few hundred thousand to a million or more dollars. CT apparatus have gone through several "generations" that involve basic changes in the scanning procedures and image format. Most data processing software is described in brochures as "proprietary". Processing speed of software is often used as a major selling point by the manufacturers. Observational strategies for data taking and processing are intimately coupled, but the devices do use general purpose programmable computers, in part. The method disclosed here dramatically reduces the image processing time. In current machines more time is spent analyzing data than collecting it, say 4 seconds to acquire the scan versus 30 seconds to process. Some recently described devices acquire data even more rapidly. A high speed processing capability would alter clinical practice of CT by allowing routine real time views of scans. Present practice is to obtain several scans, say 20 in adjacent planes of a patient, to complete a procedure, but to analyze only a few scans while the patient is present, in order to save time. Data analysis occurs at off-peak times, with images viewed by the radiologist at a later time. Also, there is no unique "best" way to reconstruct tomographic data. Radiologists choose from a menu of possible approaches depending on the procedure or feature being scanned. All approaches use the generic filtered backprojection method, but in different implementations chosen to highlight various features of the image. With our faster method such choices could be explored far more quickly, giving greater flexibility and insight to the physician. Thus, rapid reconstruction algorithms appear to be of commercial and diagnostic value to medical CT.

To generate accurate tomographic images, sufficiently noise-free data must be obtained along a sufficient number of independent coplanar paths through the target (See Shepp, L. A. and B. F. Logan, 1974, "The Fourier Reconstruction of a Head Section", IEEE Trans. Nucl. Sci., vol. NS-21, pp. 21–43). Observational paths can be labeled according to their view angle $\phi$ and impact parameter $t_1$, with respect to coordinates fixed in the target, as shown in FIG. 1. The choice of paths on which to acquire data is somewhat arbitrary, but two methods are in common use. In medical tomography measurements are typically obtained with a fixed set of detectors located along a ring surrounding the patient, as shown in FIG. 2. The X-ray source rotates about the ring, illuminating a series of detectors opposite the source with a fan beam of radiation. The opening angle of the X-ray beam is broad enough so that the fan of paths from source to detector completely encompasses the target. For accurate reconstruction of the entire target, the range of impact parameters must span the diameter of the target and the angular rotations must span at least one half of a complete rotation. We refer to the mode of operation shown in FIG. 2 as fan beam geometry. In another acceptable mode of operation the target is illuminated along a set of parallel, coplanar paths at a series of view angles. We refer to this mode of operation as plane parallel geometry. FIG. 3 illustrates this type of illumination.

Along a specific path, labeled by its view angle and impact parameter, the detector measures the transmitted intensity $I_T(t_1,\phi)$. For analysis the measurement of transmitted intensity must be converted into a measure of beam attenuation, or optical depth, along the path, given by $P(t_1,\phi) = \ln[(I_o(t_1,\phi)/I_T(t_1,\phi)]$ where $I_o(t_1,\phi)$ is the intensity incident on the target before attenuation. $P(t_1,\phi)$ is referred to as a "projection". The intensity of the unattenuated beam must be established by a separate calibration of the apparatus.

The goal of tomographic procedures is to convert the projection data into an image of the attenuation coefficient in the observed plane of the target. In its raw form the data simply provides shadow images of the target as viewed from many angles. It is not readily apparent how to locate or quantify absorbers in the plane of the target directly from the data. Only by using a reconstruction procedure can the data be combined to produce an image of the target. Thus, tomographic apparatus requires an inversion or reconstruction method.

In a typical commercial CT apparatus the reconstruction is produced in digital format and displayed as an image defined on a two dimensional grid containing, perhaps, 500 rows by 500 columns, or 250,000 elements. The data from which the image is reconstructed consist of a comparable, but even larger set of projection measurements. For this reason general purpose programmable digital computers or special purpose computers are used to store data, convert measurements of intensity to measures of attenuation, and to carry out the procedural steps of the reconstruction method.

Initial reconstruction methods for medical tomography used an iterative procedure (see U.S. Pat. No. 3,778,614). Starting with an arbitrary initial trial solution, the method computationally derived values for projection data that would occur from the trial image. Differences between the measured and derived projection data were used to correct the trial image successively, until sufficient agreement obtained between computed and observed projection.

Later the far better method of Convolution Backprojection, also referred to as Filtered Backprojection (FBP), was developed and applied in tomography apparatus (See Shepp, L. A. and B. F. Logan, 1974, "The Fourier Reconstruction of a Head Section", IEEE Trans. Nucl. Sci., vol. NS-21, pp. 21-43, and LeMay, C. A. G., 1975, U.S. Pat. No. 3,924,129). Filtered backprojection has become the universally practiced method for commercial tomographic reconstruction. FBP is better than the iterative method: first, because it can be demonstrated by mathematical analysis that FBP produces images that approximate the true image of the attenuation coefficient in the target, and second, because the computational effort required to invert the data using FBP is smaller than in the iterative method. With FBP the number of computational steps required to invert the data is known in advance, while with the iterative method the number of iteration cycles required to produce an acceptable image is not known in advance.

Furthermore, Shepp, L. A. and B. F. Logan, 1974, "The Fourier Reconstruction of a Head Section", IEEE Trans. Nucl. Sci., vol. NS-21, pp. 21-43, and Chesler, D. A., S. J. Riederer, and N. J. Pelc, 1977, "Noise Due to Photon Counting Statistics in Computed X-Ray Tomography", Journal of Computer Assisted Tomography, vol. 1, pp. 66-74 were able to analyze qualitatively the degree of noise amplification introduced by filtered backprojection. Real projection data are not measured with infinite accuracy. Noise in the data leads to noise in the reconstruction. The ratio between the relative accuracy of the reconstruction and the relative accuracy of the data defines the amplification factor. Typically, the amplification factor can be as large as ten for medical scale images. FBP methods allow one to assess the noise level required in the data to produce images of specified accuracy. The noise level in a FBP reconstruction can be lowered by incorporating low-pass filtering into the basic FBP algorithm. Filters allow noise levels to be adjusted, but at the expense of degrading resolution somewhat. Filtered reconstructions correspond to images that are averaged over neighboring regions in order to reduce noise, but the smoothing of noise results in lower resolution. Without filtering of some sort medical images tend to be unacceptably noisy.

The present invention includes the step of inversion of tomographic data that can be used to obtain images far more rapidly than is possible using filtered backprojection, while still producing images of comparable quality.

SUMMARY OF THE INVENTION

The present invention is a method for examining at least a portion of an object using penetrating radiation. The method includes the steps of transmitting radiation from an external source through the object in a plurality of coplanar rays, detecting the attenuated transmitted radiation after it has passed through the object, determining the projection data for said rays, and inverting said projection data to generate the distribution of the attenuation coefficient, wherein said inverting step includes the Direct Fourier Inversion Method such that the projection data is padded and the Fourier coefficients are filtered.

BRIEF DESCRIPTION OF THE DRAWINGS

FIG. 1 shows the geometry defining a path through the observed plane of a target. The path L between the source S and detector D is defined by its impact parameter $t_1$ and angle $\phi$ with respect to a set of fixed cartesian axes $(x_1,x_2)$ in the target.

Here the dark oval represents the skull, with a density level 2.0, while outside the skull the density is O. Inside the skull gray scales have been adjusted so that white corresponds to density 0.98 and black to density 1.04. The side panel illustrates the density variation, in arbitrary but absolute units, along a line through the three dark tumors arranged horizontally just below center in the density map.

Figure 6:
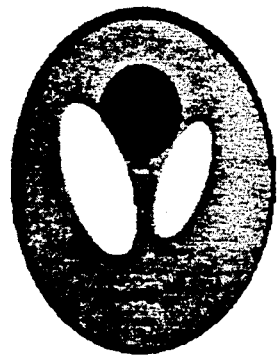
FIG. 6 shows the distribution of X-ray attenuation coefficient, which is roughly proportional to density, in a mathematical representation of a head section defined on a map of 256×256 pixels (as in Shepp, L. A. and B. F. Logan, 1974, The Fourier Reconstruction of a Head Section, IEEE Trans. Nucl. Sci., NS-21, pp. 21-43).
Figure 6:
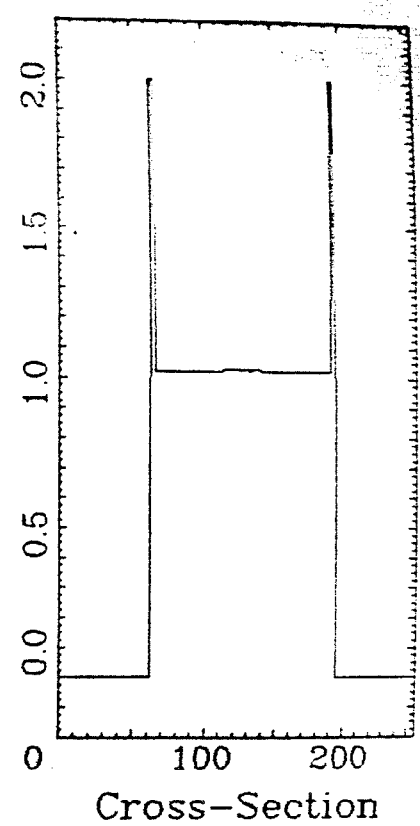
Figure 7:
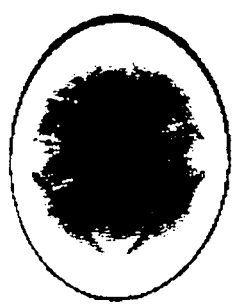
Figure 7:
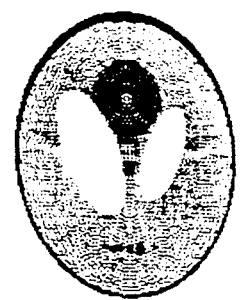
Figure 7:
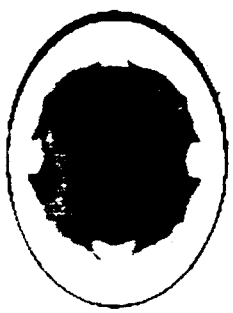
Figure 7:

FIG. 7 shows a series reconstructions of simulated tomographic data for the head section shown in FIG. 6. The four panels illustrate the straightforward implementation of DFI method and various steps that improve its performance. The result labeled DFI+-PAD+FILTER gives a reconstructed image of high quality, while reconstruction combining just PAD or just FILTER with basic DFI are not of high quality.

FIG. 8 compares the TARGET head section shown in FIG. 6 with reconstructions created using FBP and the improved DFI method described here.

Figure 9:
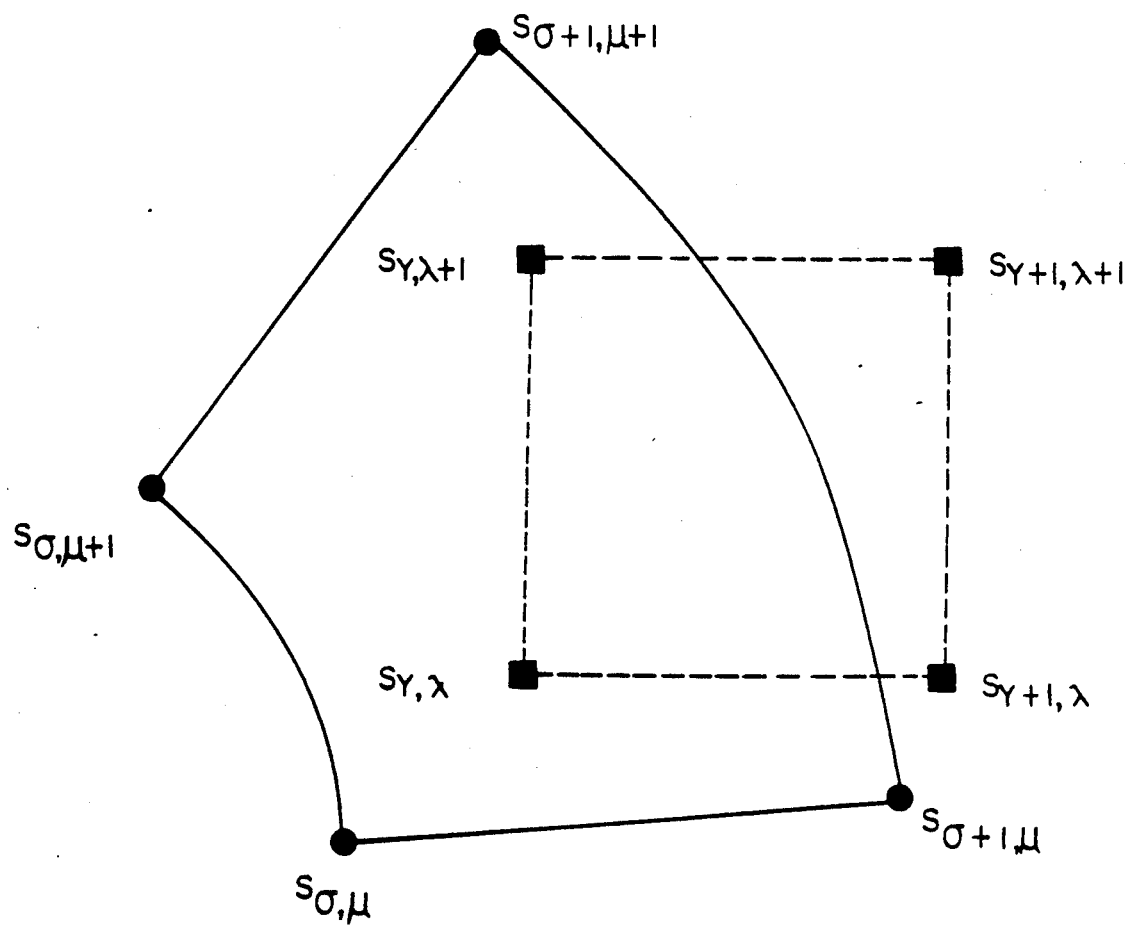

FIG. 9 depicts the geometry of the L=4 interpolations scheme described as part of the technical basis of the invention. At each Cartesian frequency $s_{\gamma\lambda}$, the Fourier transform $\tilde{F}_c$ is approximated by linear interpolation in $\tilde{F}_P$ at the four polar frequencies forming a tile surrounding $s_{\gamma\lambda}$.

Figure 10:
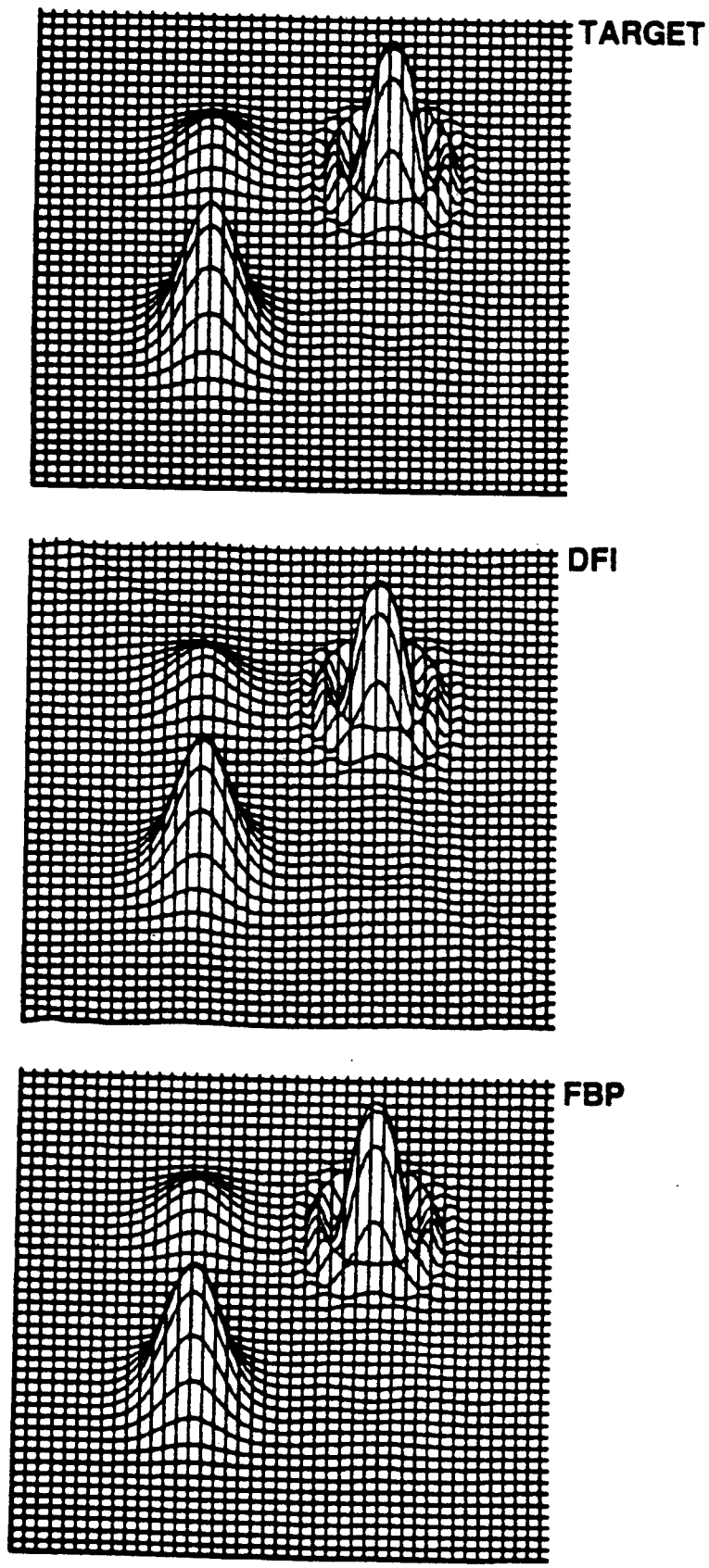

In FIG. 10 we give perspective plots of a target and its reconstruction by the basic DFI algorithm, (41), and by filtered backprojection. The functions plotted are defined to be constant on each of $256 \times 256$ square pixels. Reconstructions were obtained from simulated scan data at N=256 impact parameters and M=400 angles, as described in the text. The filtered backprojection reconstruction used the algorithm of Shepp and Logan with their filter function $\phi$. (See Shepp and Logan, 1974, "The Fourier Reconstruction of a Head Section", IEEE Trans. Nucl. Sci. vol. NS-21, pp. 21-43).

Figure 11:
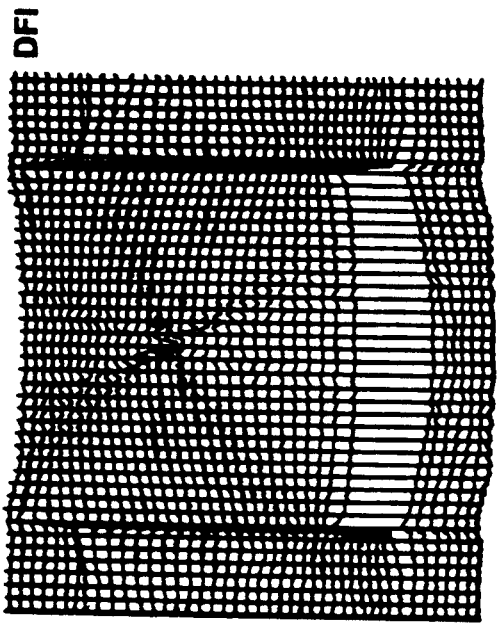
Figure 11:
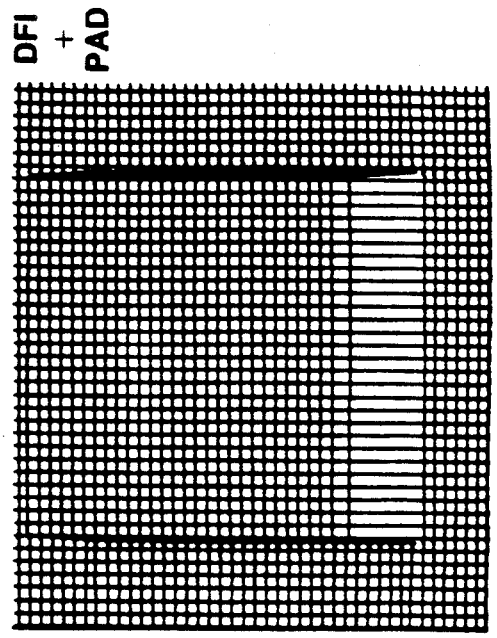
Figure 11:
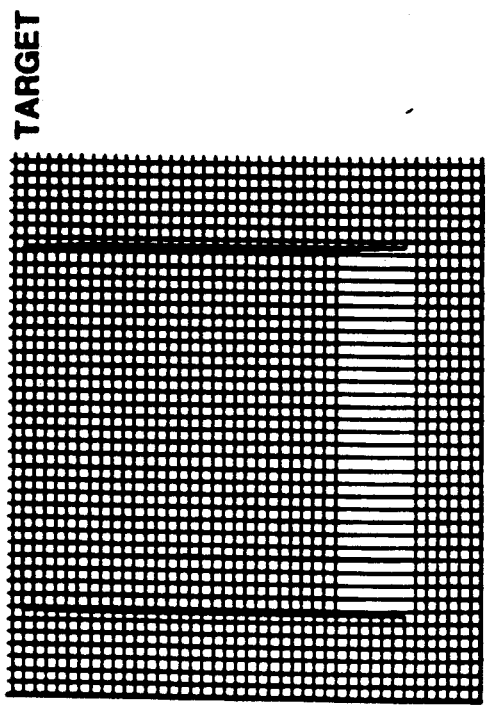
Figure 11:
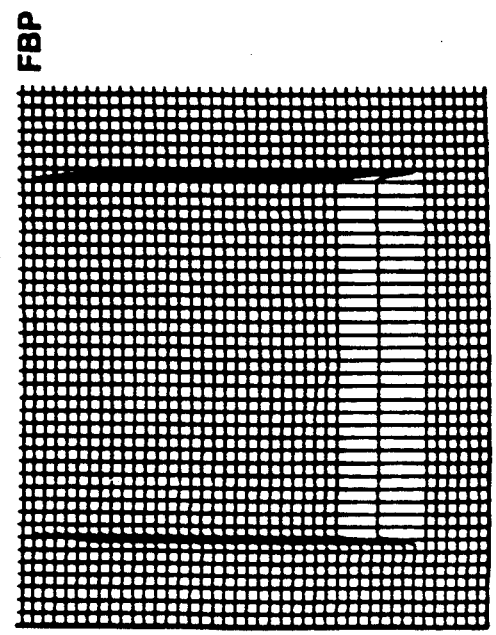

FIG. 11 shows perspective plots of a function which has value unity everywhere inside a square and zero outside. "TARGET" is the target function and "FBP" is the reconstruction by filtered backprojection, as in FIG. 10. The plots labelled "DFI" and "DFI+PAD" are, respectively, reconstructions with DFI algorithm (41) and with (41) plus padding by a factor of 8.

Figure 12:
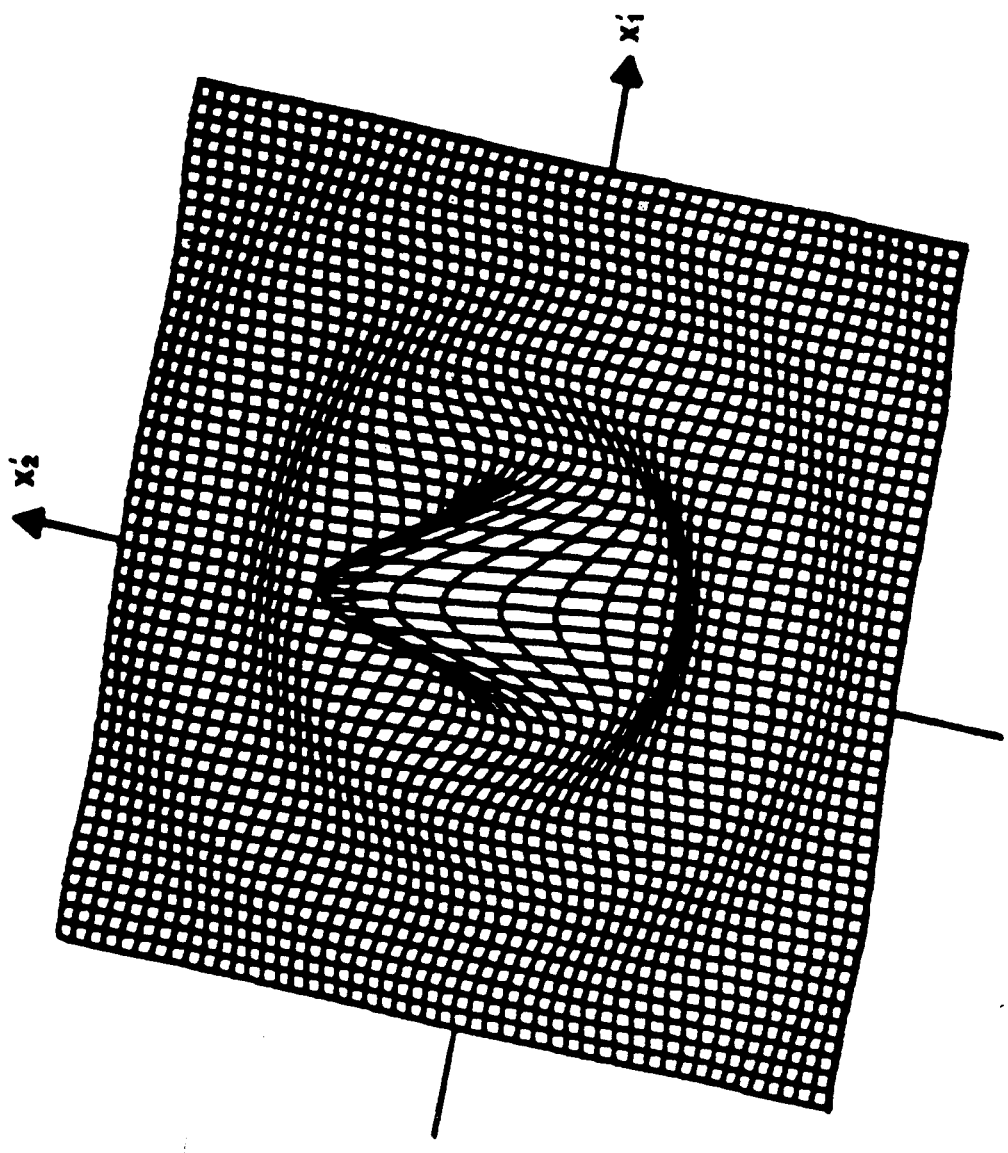

FIG. 12 is a perspective plot of the point-spread function defined by equation (43). We have plotted ReH(O x') versus x', over the range $-5\Delta t < x_1', x_2' < +5\Delta t$.

Figure 13:
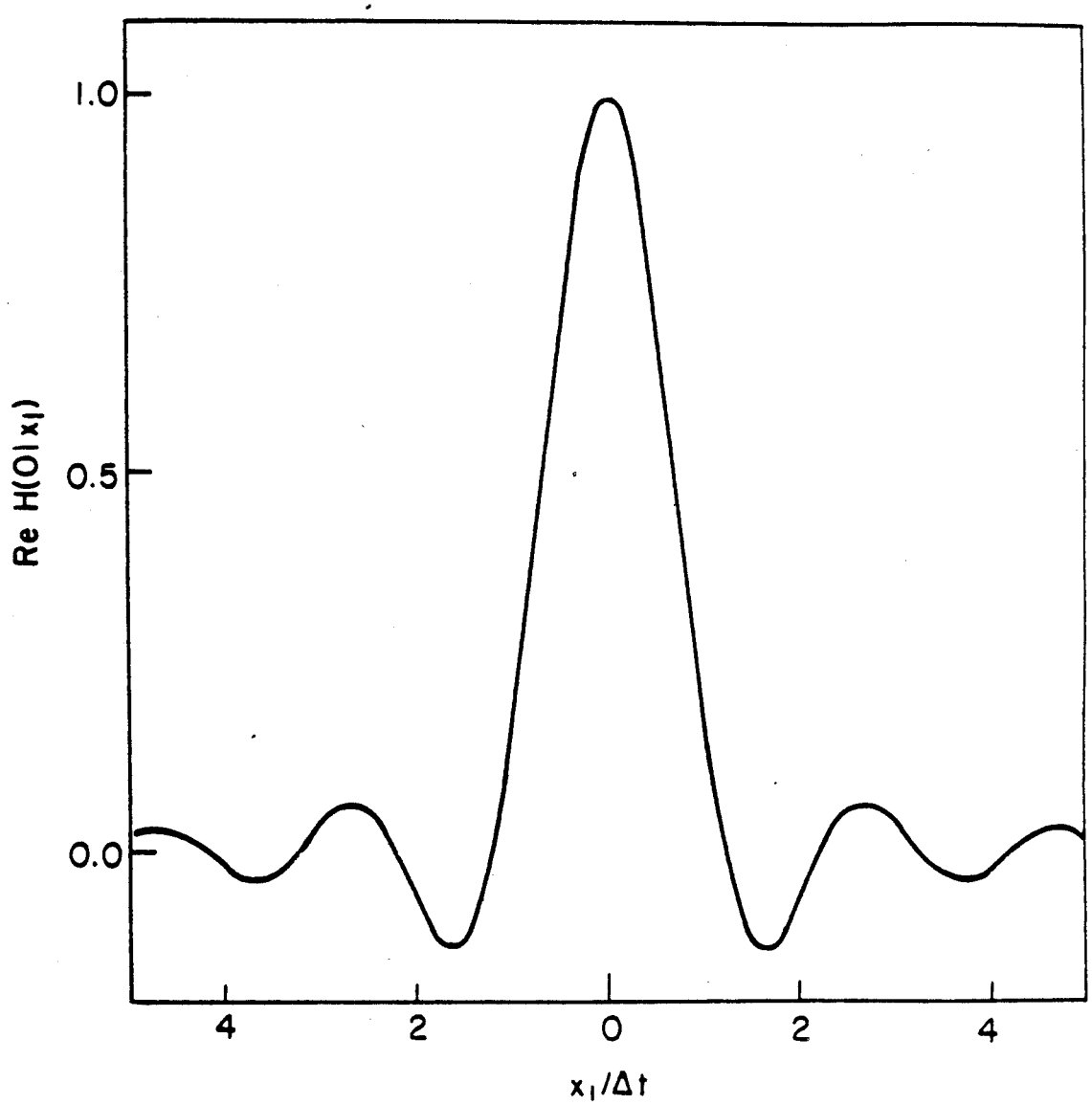

FIG. 13 gives the function ReH(O x'), as in the preceding figure, but plotted along the line $x'_2 = O$.

Figure 14:
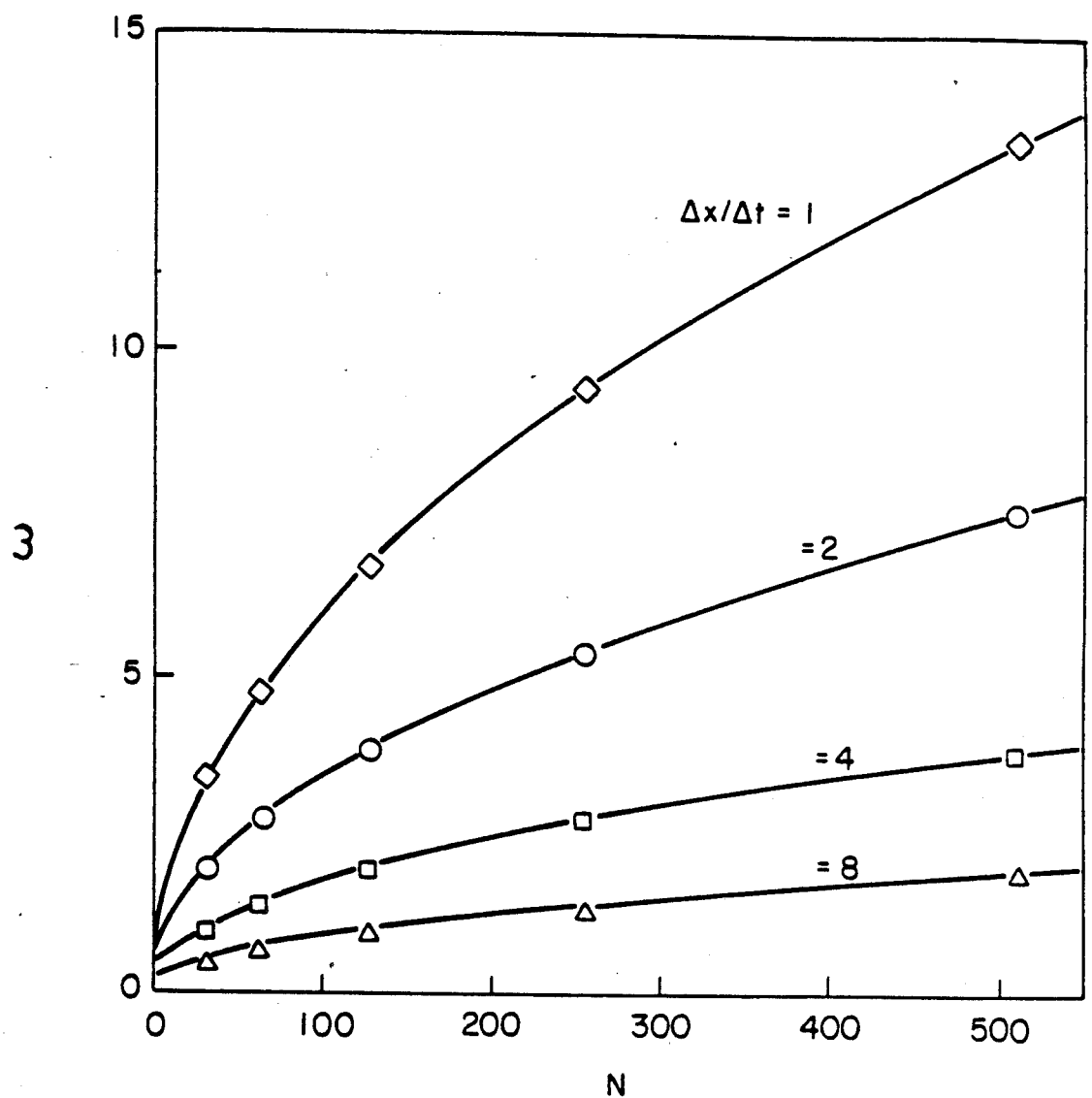

In FIG. 14 we illustrate the noise amplification factor $\omega$ for algorithm (41), defined by equation (47), for uncorrelated, random errors in the projections. The symbols depict results of the numerical simulations described in the text; solid curves are the theoretical predictions of eq. (44). The $\omega$ factor is for a K33 K reconstruction from a scan of N impact parameters by M angles. The independent variable is N. In each case we take M=100(N/64), and consider the four cases K=N (diamonds), N/2 (circles), N/4 (squares), and N/8 (triangles).

Figure 15:
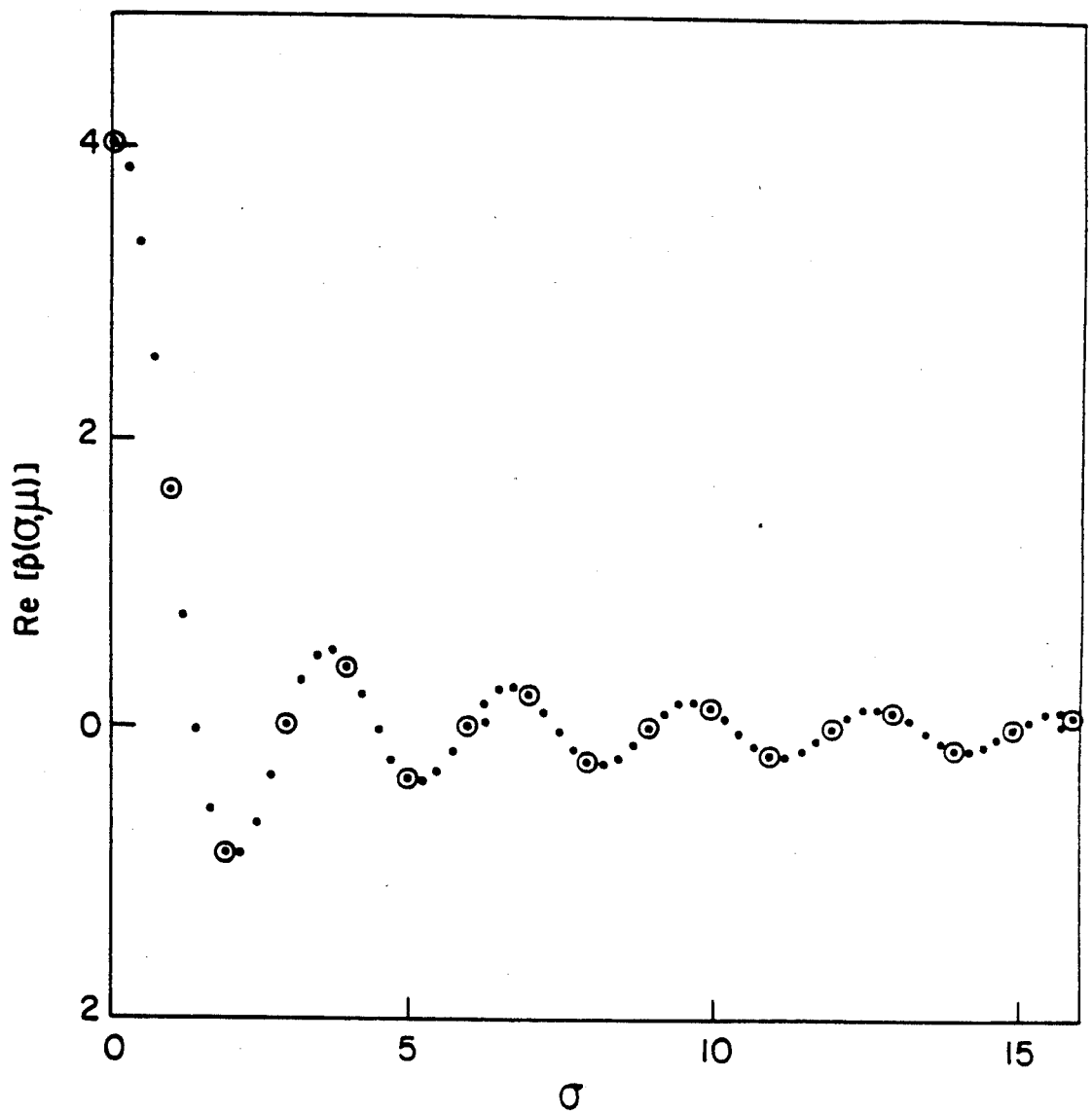

FIG. 15 is a plot of $\text{Re}\hat{p}(\sigma,\mu)$ as defined by equation (8) and computed from a simulated scan of FIG. 11 at angle $\phi = O$. The open circles are obtained when padding is omitted; the solid circles are obtained if the scan is padded with zeroes to four times its original length before computing $\hat{p}(\sigma, \mu)$.

Figure 16:
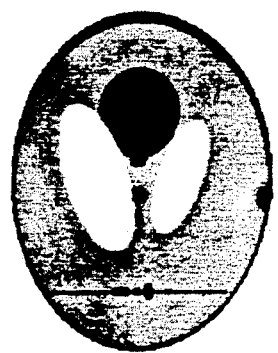
Figure 16:
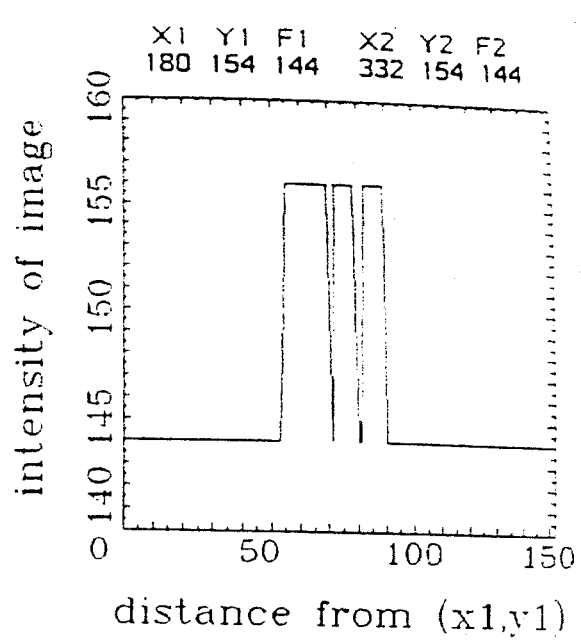

FIG. 16 shows an image of the target shown in FIG. 6 including an expanded plot of the density variation, in arbitrary absolute units, along the cross section shown drawn through the three low contrast features meant to represent tumors.

Figure 17:
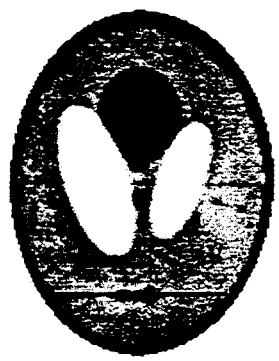
Figure 17:
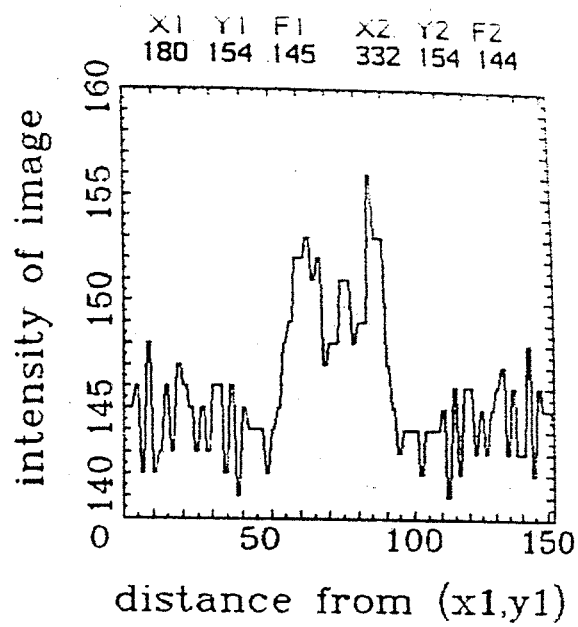

FIG. 17 shows a reconstructed image of the target as shown in FIG. 15 obtained using FBP. Note that the density variation along the cross section has become somewhat noisy.

Figure 18:
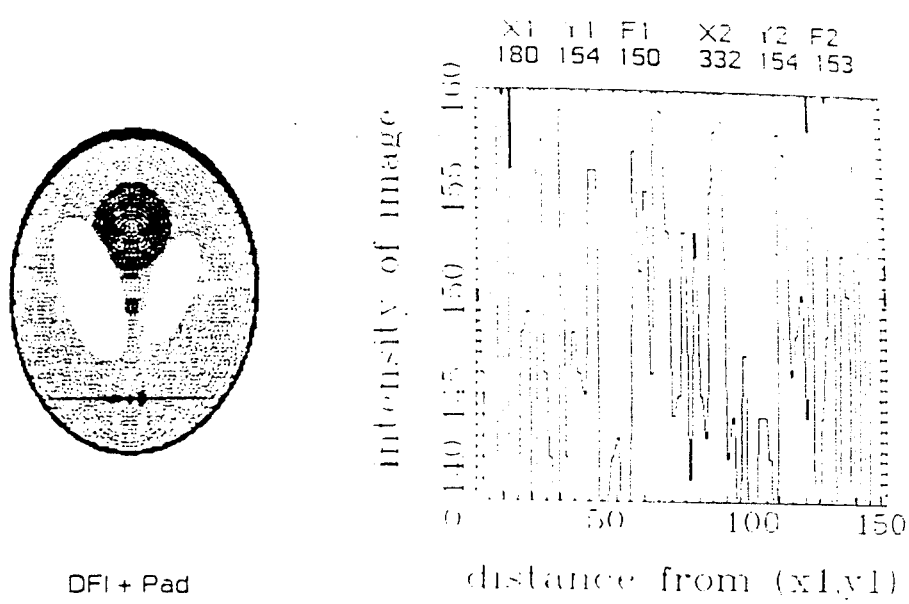

FIG. 18 shows a reconstructed image of the target as shown in FIG. 15 obtained using DFI+PAD but without filtering. Note that the density variation along the cross section has become very noisy, and the image contains serious artifacts that confuse interpretation.

Figure 19:
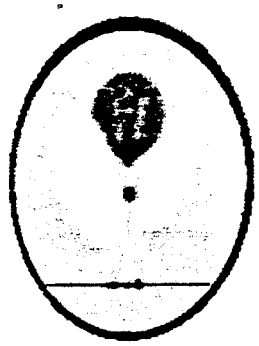
Figure 19:
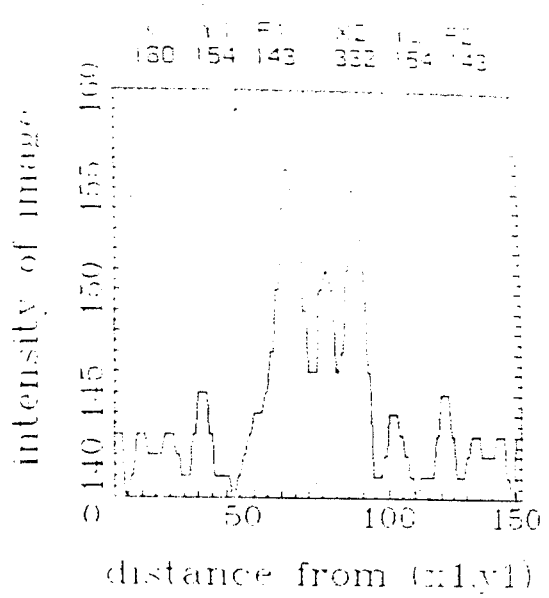

FIG. 19 shows a reconstructed image of the target as shown in FIG. 15 obtained using DFI+PAD+FILTER as disclosed here. Note that the density variation along the cross section is less noisy than shown in FIG. 16 as reconstructed using FBP. The result here appears completely comparable, or even superior, in quality to the result shown in FIG. 16.

DESCRIPTION OF THE PREFERRED EMBODIMENT

In the preferred embodiment of the present invention, radiation from an external source is transmitted through the target. Such radiation includes electromagnetic radiation such as x-rays, $\gamma$ rays or electron beams.

The attenuated transmitted radiation is detected by detectors sensitive to the type of transmitted radiation.

The projection data is obtained from the intensity of the incident and attenuated transmitted radiation.

The projected data is inverted to generate the distribution of attenuation coefficients on a rectangular grid of points.

The attenuation coefficients may be conveniently displayed on a device such as a cathode ray tube.

Figure 2:
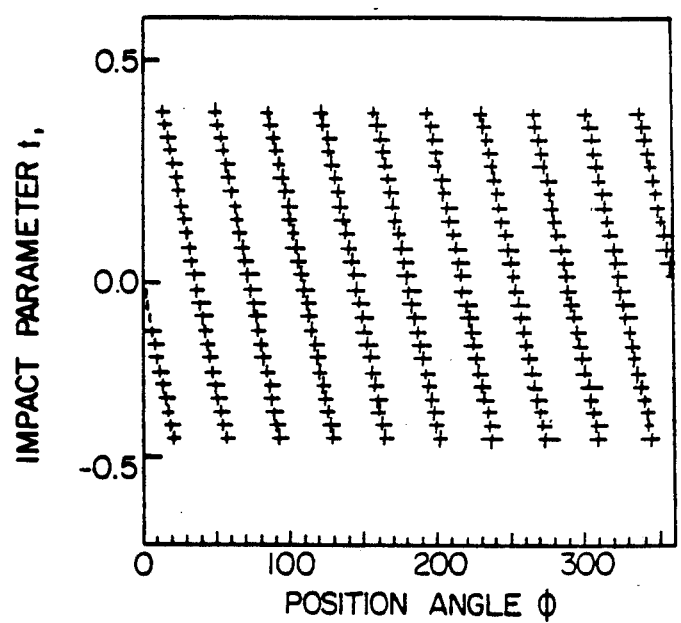
FIG. 2 is a schematic showing observational paths in a typical medical CT scanner using the "fan beam" observational mode. Discrete observational paths occur at points $(t_1,\phi)$ as shown in the upper right hand panel.
Figure 2:
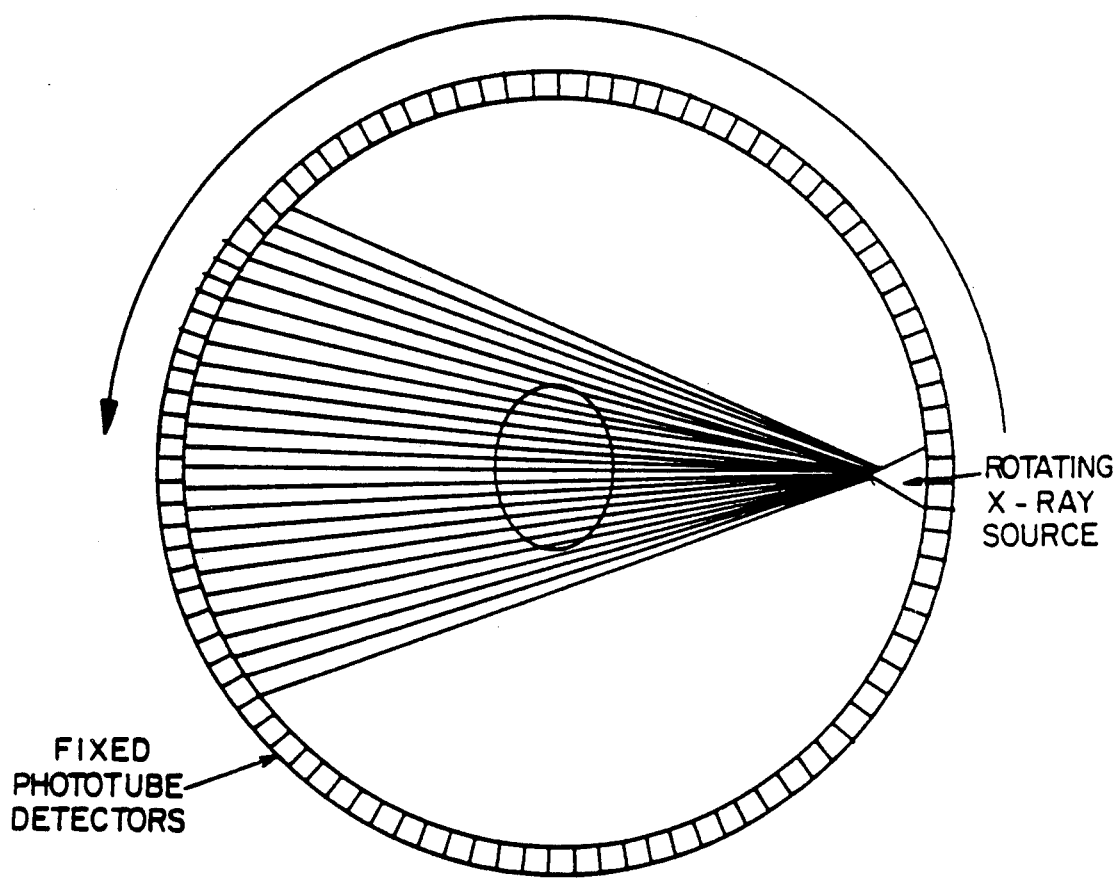
Figure 3:
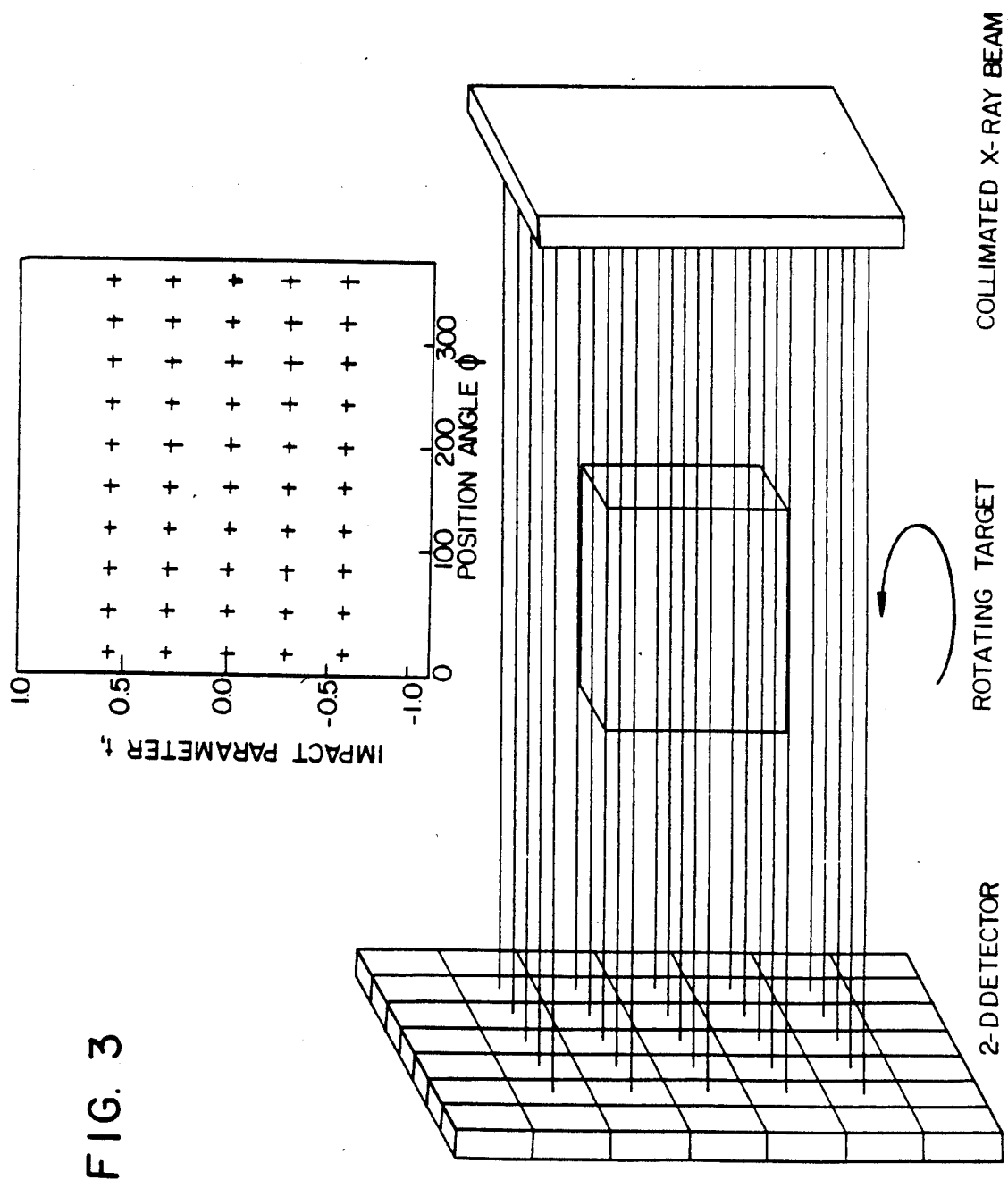
FIG. 3 is a schematic showing observational paths in a scanner using the "parallel beam" observational mode. Here a parallel, collimated beam of radiation illuminates the target in multiple stacked planes and multiple impact parameters simultaneously. The target is rotated for observations at differing view angles $\phi$. Discrete observational paths in one of the planes occur at points $(t_1,\phi)$ as shown in the upper right hand panel.
Figure 4:
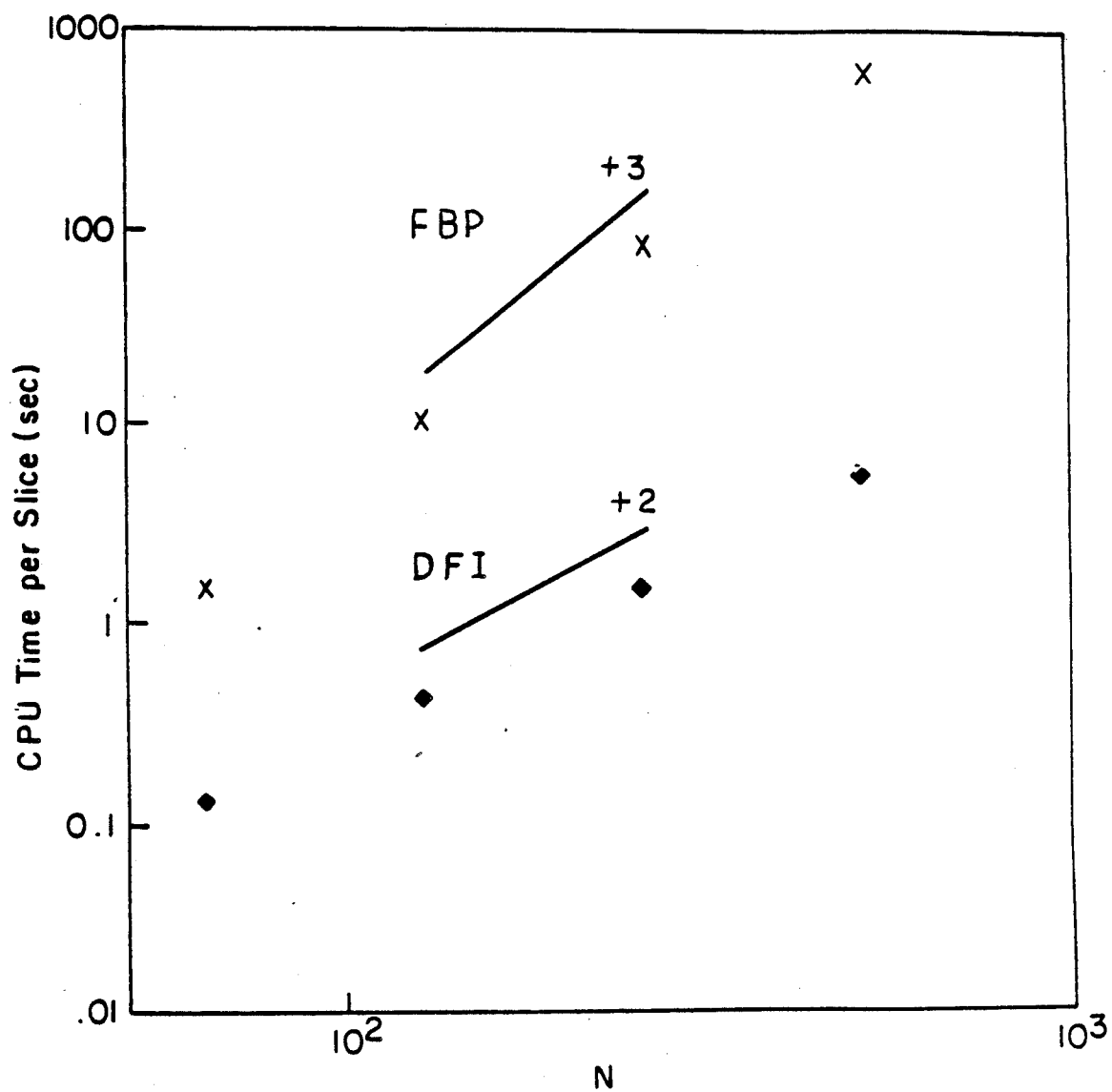
FIG. 4 shows a comparison of the computational time required to analyze tomographic data using Filtered Back Projection (FBP) and the Direct Fourier Inversion method for images of pixel size N×N. Projection data for each image size are identical, and the reconstructions were carried out using a Floating Point Systems FPS-164 Array Processor.

A method for inversion of the projection data is used to obtain images far more rapidly than is possible using filtered backprojection, while still producing images of comparable quality. Because the method applies Fourier analysis, we refer to it as the direct Fourier Inversion Method (DFI). The method is described in more detail below. Its essential advantage over FBP is that the number of mathematical operations required to invert data to form an image of size $N \times N$ pixels scales as $N \times N \times N$ in FBP but only as $N \times N \times \log_2(N)$ in the DFI method. In FIG. 4 we illustrate the time required to invert exactly identical data for images of various size using FBP and DFI, as carried out on a general purpose computer, the Floating Point Systems FPS-164 Array Processor, optimized for both methods. The DFI method inverts data 40 times faster than FBP for images containing $256 \times 256$ pixels, and its relative speed advantage grows for larger images.

The speed advantage of the DFI method has been known for many years, but until now the method has not been found to produce images of acceptable quality for arbitrary targets. Especially in some medical applications, where the goal is to discover small features of low contrast in soft tissue, e.g. tumors in the brain where the image must reveal features with 1% contrast, the quality of former realizations of the DFI method was totally unacceptable. Inferior image quality, with respect to FBP, arises from artifacts and noise amplification introduced by inaccurate interpolation required in standard DFI methods, as described below. As we disclose, certain combinations of improvements in the DFI method allow us to produce acceptable images while still maintaining an enormous speed advantage over FBP.

In the published literature there exist many discussions of DFI methods, some of which use approaches close to those discussed here. For example see the discussions in the review article by Lewitt, R. M., 1983, "Reconstruction Algorithms: Transform Methods", Proc. IEEE, vol. 71, pp. 390–408, and the papers by Mersereau, R. M., and A. V. Oppenheim, 1974, "Digital Reconstruction of Multi-Dimensional Signals from their Projections", Proc. IEEE, vol. 62, pp. 1319–1338, Stark, H., J. W. Woods, I. Paul, and R. Hingorani, 1981, "An Investigation of Computed Tomography by Direct Fourier Inversion and Optimum Interpolation", IEE Transactions on Acoustics, Speech, and Signal Processing, vol. ASSP-29 pp. 237–245, Low, K.-H., and F. Natterer, 1981, "An Ultra-Fast Algorithm in Tomography", Tech. Rept. A81/03, Fachbereich Angewandte Mathematik und Informatik, U. des Saarlandes, 6600 Saarbrucken, West Germany, and Niki, N., T. Mizutani, Y. Takahashi, and T. Inouye, 1983, "High-Speed Computerized Tomography Image Reconstruction Using Direct Two-Dimensional Fourier Transform Method", Systems. Computers. Controls, vol. 14, pp. 56–65. We have examined the methods discussed in these papers and found that, for some applications, none of them produces images comparable in quality to filtered back-projection. Furthermore, none of the previous studies of DFI includes an analysis of noise amplification. To date no published discussions of DFI methods combine the elements that we disclose here, that do produce high quality images even for medical applications which are particularly difficult for DFI methods. Below we discuss a novel DFI method, combining some of the features of earlier work, that produces high-quality images with acceptable noise amplification.

Mathematical analysis shows that the two dimensional Fourier Transform of the target and the one dimensional Fourier Transforms of the projected images of the target are identical. This result, known as the Projection-Slice theorem, applies to exact continuous representations of the target and its projections. In practical applications tomography works with noisy discrete measurements of projections. The limitation to discrete data complicates, but does not invalidate the general mathematical analysis. From the projection data it is straightforward to determine (approximately) the Fourier coefficients of the target along a series of discrete points arranged on a polar raster: coefficients are given at equally spaced points along sets of rays from the coordinate origin in frequency space. However, to carry out a reconstruction efficiently it is necessary to know the Fourier coefficients along sets of points distributed in frequency space in a Cartesian raster. Thus, efficient Fourier methods in tomography require a procedure for interpolation from a polar raster to a Cartesian raster. Inaccurate interpolation produces artifacts in the image, and can result in noise amplification. Highly accurate interpolation methods can be used, but they tend to require such intensive computation that the Fourier method loses its speed advantage over FBP. One of the improvements to the DFI methods occurs from improvements to the interpolation technique.

Fourier methods achieve computational efficiency when they are able to make use of the so called Fast Fourier Transform algorithm (FFT). To use the FFT, data must be available at equally spaced intervals on a Cartesian grid, and, for most rapid implementation, the number of points should equal some power of two, i.e. 2, 4, 8, 16, 32, . . . Fast Fourier transform methods can be devised without the limitation that the number of points equals some power of two. However, in practice the number of points can easily be adjusted to equal a power of two by padding, as described below.

An important detail of the method is that values for Fourier coefficients depend on the coordinate origin chosen for the spatial measurements. Computationally, different choices of origin introduce progressive phase shifts that can be accounted for by multiplying the Fourier coefficients by a known phase shift factor. In order to achieve the computational advantage offered by the FFT we obtain discrete transforms in which the origin corresponds to the first element. However, to apply results of the slice-projection theorem, especially in the interpolation step described below, it is necessary to shift all transforms so that the origin corresponds to a common point in the target. That origin is given by the point at which the rotation axis defining the view angles intercepts the target plane. We refer to coefficients obtained by the FFT as Discrete Fourier Transform coefficients (DFT), while coefficients altered by phase shift to the natural center of the target are referred to as Centered Discrete Fourier Transform coefficients (CDFT). Without the shift from DFT to CDFT origin, values for the Fourier coefficients appear to oscillate in sign from point to point, making interpolation very difficult, e.g. 1.8, −1.7, 1.6, −1.5. With CDFT coefficients values for Fourier coefficients vary much more smoothly, e.g. the previous sequence becomes 1.8, 1.7, 1.6, 1.5.

Figure 5:
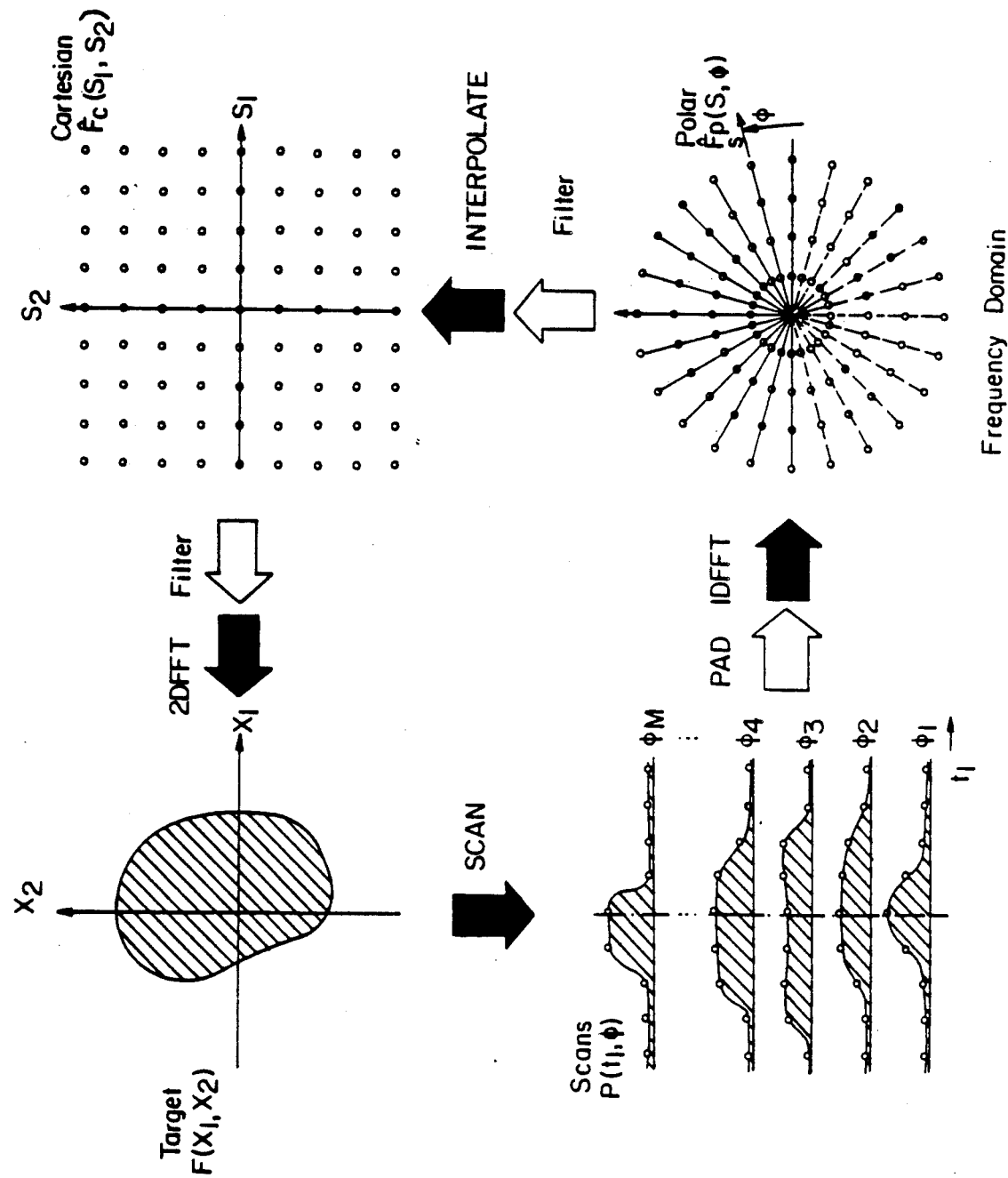
FIG. 5 is a schematic of the steps of the Direct Fourier Inversion Method showing the relation between the target and its projections in signal space, and the representations of the Fourier transform of the target in Polar and Cartesian rasters.

Steps of the DFI method are outlined in FIG. 5. Using the observed projection data we readily determine the coefficients of the Fourier Transform of the target on a set of points that are equally spaced in angle and radial position on a polar raster. We then interpolate from the polar raster onto a grid of points that are equally spaced in a Cartesian grid. Finally, we obtain the image by a two dimensional Fourier inversion.

Given a set of plane parallel projection measurements at equally spaced impact parameters and view angles the essential steps involved in the DFI method are:

BASIC STEPS OF THE DIRECT FOURIER INVERSION METHOD FOR INVERSION OF TOMOGRAPHIC DATA (1) 1D FFT: For projection data at a given angle, obtain the discrete, one dimensional Fast Fourier Transform with respect to impact parameter. The result gives Fourier coefficients along a ray in signal space at equally spaced intervals from the origin up to some maximum frequency.

(2) Phase Shift to Target Origin: Bring the phase of the coefficients obtained in (1) into agreement with a positioning convention that places the spatial coordinate origin at the axis about which the view angle was rotated.

(3) Fill Polar Raster: Repeat steps (1) and (2) for the projection data at each new view angle to build up the Fourier coefficients along a series of rays as shown in FIG. 5.

(4) Interpolate to Cartesian Grid: By interpolation determine values for the Fourier coefficients at equally spaced points in the two dimensional Cartesian grid.

(5) Phase shift to Cartesian Origin: Perform a phase shift from the origin at the target center to an origin at the lower left corner of the square region in which the image will be constructed, as required by the convention for locating the origin in two dimensional FFTs.

(6) Inverse Fast Fourier Transform: Use the inverse FFT to convert from the frequency domain of the Fourier Transform back to signal space producing an image of the target.

In the basic form described above in steps 1-6 the DFI method can produce acceptable images only for targets in which the attenuation coefficient varies smoothly. However, numerous studies have found that the method produces unacceptable images for practical targets, such as are found in medical applications, where sharp density variations are encountered between bone and soft tissue. Problems arise from inaccuracy in the interpolation procedure, and from the basic problem that Fourier analyses tend to produce oscillatory artifacts when they encounter sharp discontinuities. Taken together these problems introduce unacceptable distortion and artifacts into the reconstructed image.

Related problems also affect reconstructions obtained using back projection methods. In fact the low-pass filters, noted above in connection with noise amplification, also are designed to correct artifacts that would otherwise contaminate the image generated by back projection methods without filtering.

We have discovered means to improve the DFI method to such a degree that it produces acceptable images that are comparable in quality with results obtained by FBP, while still maintaining the enormous speed advantage of DFI. Those steps are labeled by the terms "padding" and "filtering" in FIG. 5.

PADDING: Prior to step (1) above we "pad" the projection data by adding additional data at impact parameters both smaller and larger than were actually observed. Since the target does not extend beyond the observed range of impact parameters, the values for the padded data do not need to be estimated; they are known exactly to be zero. Thus, by padding we are not introducing an approximation, we are using additional known information. We also use padding to assure that the number of data points in the projection are an integral power of 2, as required for optimum use of the FFT.

By padding we obtain values for Fourier coefficients at more points along the ray in the polar raster. Because we have no additional resolution the maximum distance of points from the origin in frequency space is not increased, but the number of points between the origin and the last frequency point increases by the padding factor. For instance, if we observed projection data at 256 impact parameters and padded the data by adding zeros at 256 more points, then we obtain 512 values for Fourier coefficients between the origin and the most distant point, rather than 256 without padding. Furthermore, the values at the intermediate points are approximately those values that would have been obtained using high order interpolation based on analyses of the behavior of Fourier coefficients at frequencies intermediate between discrete values. To apply those interpolation formulae at arbitrary intermediate points is possible, but computationally expensive. By padding we achieve the same accurate interpolation along rays and get points at many intermediate frequencies using the FFT algorithm itself. It is possible to adjust the amount of padding to meet the needs of the particular target being analyzed. By this step the interpolation procedure becomes far more accurate.

FILTERING: In order to remove or minimize the artifacts corresponding to oscillations introduced by using Fourier methods, a number of standard low pass digital filters have been developed. We find that the use of a standard low pass filter, e.g. the Hanning filter with adjustable cutoff frequency, effectively removes high frequency oscillations in the image. The Hanning filter smoothly reduces the amplitude of the Fourier coefficients by a factor $Y(s)$ that varies smoothly from 1 to 0 as frequency grows from O to $s_c$:

$$Y(s) \equiv \begin{cases} \frac{1}{2}(1 + \cos(\pi s/s_c)] & \text{if } s < s_c \\ 0 & \text{if } s > s_c \end{cases}$$

By choice of $s_c$ one can selectively adjust the cutoff of high frequency variations. (Note that the choice of low-pass filter in FBP methods serves the identical purpose). Filtering can be applied to the Fourier coefficients in either the polar or Cartesian grid, or both. Filtering essentially corresponds to averaging the reconstruction over length scales inversely proportional to the cutoff frequency. Viewed in this way it can readily be shown that filtering sacrifices resolution in order to improve the relative accuracy of values for the X-ray attenuation coefficient in the reconstruction. The choice of cutoff frequency $s_c$ can be chosen to adjust the degree of smoothing selectively.

It should be noted that the choices of filters can result in additional computational savings. It is unnecessary to evaluate Fourier coefficients beyond the cutoff frequency, or to carry out the inverse Fourier Transform for an unnecessarily large set of coefficients. For example, suppose that data was obtained sufficient to reconstruct the image on a grid of 512×512 pixels, corresponding to a maximum frequency s(512), but that it is determined that the filter step needs to eliminate $\frac{1}{2}$ the frequencies. Then the Fourier coefficients in the Cartesian grid need only fill an array of 256×256 points and the inverse transform can be carried out more rapidly using the smaller set 256×256 Fourier coefficients.

A novel method for generating a representation of attenuation coefficient of a target given measurements of the projection data, as defined above, for set of equally spaced impact parameters and equally spaced view angles is obtained by adding to the list of processing steps described above the following

ADDITIONS TO THE BASIC STEPS OF THE DIRECT FOURIER INVERSION METHOD (A1) PAD: Before Step 1, above, given the projection data for a set of impact parameters at a given view angle, add additional data points with zero attenuation at impact parameters both larger and smaller than the observed ones.

(A2) APPLY POLAR FILTER: Between Steps 2 and 3 above, apply a low-pass filter to the Fourier coefficients, by multiplying the coefficients by an appropriate factor at the given radial frequency. In practice steps A2 and 2 are combined in a single multiplication to produce filtering and phase shift.

(A3) APPLY CARTESIAN FILTER: Between Steps 5 and 6 above, apply a low-pass filter to the Fourier Coefficients (in Cartesian coordinates), by multiplying the coefficients by an appropriate factor at each frequency. In practice step A3 and 5 are combined in a single multiplication to produce filtering and phase shift.

We now show examples of reconstructions that illustrate the performance of the DFI method described and compare that method with FBP. For the examples we use mathematically defined targets with known distribution of X-ray attenuation coefficient. Simulations of tomographic data were generated by numerical simulation as described below in detail. FIG. 6 shows a target representing typical density variation in a medical head section. This particular target, or phantom, was used by Shepp, L. A., and B. F. Logan, 1974, "The Fourier Reconstruction of a Head Section", IEEE Trans. Nucl. Sci., vol. NS-21, pp. 21-43 to illustrate the FBP method. As shown in one panel of FIG. 6, the features of interest in a head section are very low contrast areas in soft tissue. In particular, FIG. 7 shows how the additional steps of padding and filtering result in a dramatic improvements in the image quality of DFI reconstructions. FIG. 8 illustrates how DFI compares with FBP.

TECHNICAL BASIS OF THE INVENTION

In this section we present a detailed analysis of the DFI method, the results of which form the basis for the technical innovations described above. Part (a) describes the DFI method precisely, using assumptions and notation used throughout the rest of this section. Part (b) shows how a DFI reconstruction can be written as a linear function of the projection data, with weighting coefficients whose values are given explicitly in terms of a certain function. In part (c) we derive the operations count, the number of arithmetic operations required to obtain one DFI image reconstruction from the appropriate data. Part (d) introduces the point-spread function, which allows us to deduce an approximate relationship between the exact target and its DFI reconstruction. In part (e) we analyze noise amplification and in part (f) we derive a DFI algorithm comparable in quality to filtered backprojection.

(a) Basic Steps of the Direct Fourier Inversion Method

Consider a real-valued function $F(x)$ whole domain is a compact subset T of $R^2$ (FIG. 1). We assume that T is contained within a circle of radius R. The fundamental problem in computed tomography is to determine F from a set of line integrals of the form $$P(t_1, \phi) = \int_L dt_2 F(x_1, x_2), \quad (1)$$

where the integration is along ray L in FIG. 1 and the variables $(t_1, t_2)$ are related to $(x_1, x_2)$ by the orthogonal transformation $$\begin{bmatrix} x_1 \\ x_2 \end{bmatrix} = \begin{bmatrix} \cos\phi & -\sin\phi \\ \sin\phi & \cos\phi \end{bmatrix} \begin{bmatrix} t_1 \\ t_2 \end{bmatrix} \quad (2)$$

As the viewing angle, $\phi$, and impact parameter, $t_1$, take on values $0 \leq \phi < \pi$ and $-R < t_1 < R$, the set of all rays in T is sampled.

The inversion of (1) to give F in terms of P may be carried out formally in a number of ways. Consider, for example, the Fourier transform of P with respect to $t_1$:

$$\hat{P}(s,\phi) = \int_{-\infty}^{+\infty} dt_1 \, P(t_1, \phi) \, e^{-2\pi i s t_1}, \quad (3)$$

for $-\infty < s < +\infty$. Using (1) to write P in terms of F, and (2) to transform the integration variables to $(x_1, x_2)$, we obtain the Central-Slice Theorem:

$$\hat{P}(s,\phi) = \int_{-\infty}^{+\infty} \int_{-\infty}^{+\infty} dx_1 dx_2 F(x_1, x_2) \, e^{-2\pi i (x_1 s \cos\phi + x_2 s \sin\phi)} \quad (4)$$

(See Mersereau, R. M., and A. V. Oppenheim, 1974, "Digital Reconstruction of Multi-Dimensional Signals from their Projections", Proc. IEEE, vol. 62, pp. 1319-1338, and Shepp, L. A. and B. F. Logan, 1974, "The Fourier Reconstruction of a Head Section", IEEE Trans. Nucl. Sci., vol. NS-21, pp. 21-43). Thus $P(s,\phi)$ equals $F_F(s,\phi)$, the Fourier transform of F in polar frequency coordinates $(s,\phi)$. The inverse transform is the formal solution:

$$F(x_1, x_2) = \int_{-\infty}^{+\infty} \int_{-\infty}^{+\infty} ds_1 ds_2 \hat{P}\left[\sqrt{s_1^2 + s_2^2}, \tan^{-1}\left[\frac{s_2}{s_1}\right]\right] e^{+2\pi i (x_1 s_1 + x_2 s_2)} \quad (5)$$

where we have introduced the cartesian frequency coordinates $(s_1, s_2) = (s \cos\phi, s \sin\phi)$.

In practice the inversion is performed from discrete data. In plane parallel tomography, we measure the quantities $P(t_{\tau\mu})$, where $$(t_1, \phi)_{\tau\mu} = (\tau\Delta t, \mu\Delta\phi) \text{ for } \frac{-N}{2} \leq \tau \leq \frac{N}{2} \text{ and } 0 \leq \mu < M \quad (6)$$

Thus the sampling increments are $\Delta t = 2R/N$ and $\Delta\phi = \pi/M$, where the parameters N and M determine the total number of measurements, NM.

Equations (3)-(5) illustrate the essential difficulty encountered in practice: If the function F is arbitrary, then a discrete set of data provides insufficient information carry out the integration in (3) and, hence, the inversion. To proceed one generally introduces some a priori information about F. Here we adopt the standard assumption that F is band-limited, $$\hat{F}_p(s,\phi) = 0 \text{ if } |s| \geq s_c \quad (7a)$$

and Nyquist-sampled $$\Delta t < 1/(2s_c) \quad (7b)$$

with finite scalar bandwidth $s_c$. Equations (7) are a set of uncontrolled assumptions that, strictly speaking, cannot be valid if R is finite. Nevertheless, it seems reasonable to assume that a set of measured projections is band-limited, by virtue of the finite resolving power of any measuring apparatus (See, e.g., D. Slepian, 1976, "On Bandwidth", Proc. IEEE, vol 64, pp. 292-300).

Equation (7) and the Shannon sampling theorem guarantee that the discrete Fourier transform of $P(t_{\tau\mu})$, $$\hat{p}(\sigma,\mu) = \Delta t \sum_\tau P(t_{\tau\mu}) e^{-\frac{2\pi i}{N}\sigma\tau}, \qquad (8)$$

equals the continuous transform $F_p(s_{\sigma\mu})$ at the $M \times N$ "polar frequencies"

$$(s,\phi)_{\sigma\mu} = \left(\frac{\sigma}{N\Delta t}, \mu\Delta\phi\right) \text{ for } \frac{-N}{2} \leq \sigma < \frac{N}{2} \text{ and } 0 \leq \mu < M \qquad (9)$$

In sums where no limits appear, e.g. (8), it is implied that the summation variable runs over its entire domain. Here $\tau$ runs from $-N/2$ to $N/2-1$ inclusive]. Altogether the frequencies $s_{\sigma\mu}$ form a uniform polar raster, as shown in FIG. 5.

The DFI method interpolates in this grid to obtain $\tilde{F}_c(s_{\gamma\lambda})$, the transform of F on a uniform cartesian raster of $K^2$ "cartesian frequencies"

$$(s_1, s_2)_{\gamma\lambda} = \frac{1}{K\Delta x}(\gamma,\lambda) \text{ for } \frac{-K}{2} \leq \gamma,\lambda < \frac{K}{2} \qquad (10)$$

Here K is an int and $\Delta x$ has the same units at $t_l$. The tilde on $\tilde{F}(\hat{s}_{\gamma\lambda})$ implies that interpolation generally produces an approximation to the exact transform $\hat{F}_c(s_{\gamma\lambda})$.

Finally, the inverse discrete transform of $\tilde{F}_c(s_{\gamma\lambda})$ gives an approximation to F, $$\tilde{F}(x_{\alpha\beta}) = \frac{1}{(K\Delta x)^2} \sum_\gamma \sum_\lambda \tilde{F}_c(s_{\gamma\lambda}) e^{+\frac{2\pi i}{K}(\alpha\gamma+\beta\lambda)} \qquad (11)$$

$K^2$ points separated by $\Delta x$ on a uniform raster:

$$(x_1, x_2)_{\alpha\beta} = \Delta x(\alpha,\beta) \text{ for } \frac{-K}{2} \leq \alpha,\beta < \frac{K}{2}. \qquad (12)$$

If the interpolation scheme happens to be exact, i.e. $\tilde{F}_c(s_{\gamma\lambda}) = \hat{F}_c(s_{\gamma\lambda})$, then it follows from the sampling theorem in frequency space that the reconstruction is also exact, provided $F_c$ is Nyquist-sampled by the cartesian frequency grid. This amounts to the requirement that $$K\Delta x \geq N\Delta t \qquad (13)$$

The basic steps in the DFI method are summarized in FIG. 5.

A particular DFI algorithm is uniquely determined by (8) and (11), a prescription for the interpolation, and by the integers N, M, and K. In view of the form of the formal solution, (5), it seems reasonable to consider linear interpolation, which may be written quite generally in the form $$\tilde{F}_c(s_{\gamma\lambda}) = \sum_\sigma \sum_\mu G(s_{\gamma\lambda}|s_{\sigma\mu}) \hat{F}_p(s_{\sigma\mu}), \qquad (14)$$

where the details of the interpolation scheme are contained in the "interpolation function" G. Thus we visualize the interpolation process as the operation of G on each input, or polar frequency, and output, or cartesian frequency, to produce an interpolation weight.

For given values of the parameters N, M, and K, equation (14) establishes a one-to-one correspondence between G-functions and DFI algorithms. Henceforth we shall refer to a particular DFI algorithm by its G-function. For example, Startk, H., J. W. Woods, I. Paul, and R. Hingorani, 1981, "An Investigation of Computed Tomography by Direct Fourier Inversion and Optimum Interpolation", IEE Transactions on Acoustics, Speech, and Signal Processing, vol. ASSP-29, pp. 237–245, introduced the algorithm $$G(s_{\gamma\lambda}|s_{\sigma\mu}) = \text{sinc}\left[\frac{s_{\gamma\lambda} - s_\sigma}{\Delta s}\right]\text{sigm}[\phi_{\gamma\lambda} - \phi_\mu] \qquad (15)$$

where $s_{\gamma\lambda}$ and $s_{\sigma\mu}$ have polar coordinates $(s_{\gamma\lambda}, \phi_{\gamma\lambda})$ and $(s_\sigma, \phi_\mu)$ respectively, $\Delta s = 1/N\Delta t$ is the radial spacing in the polar grid, and the sinc and sigm functions are defined by $$\text{sinc}(s) = \frac{\sin(\pi s)}{\pi s} \qquad (16a)$$

and $$\text{sigm}(\phi) = \frac{\sin\left(\frac{M\phi}{2}\right)}{M\sin(\phi/2)} \qquad (16b)$$

H. Stark (1979, "Sampling Theorems in Polar Coordinates", J. Opt. Soc. Am., vol. 69, pp. 1519–1525) showed that algorithm (15) is exact if assumption (7) holds and if the coefficients $c_l(s)$ in the series $$\hat{F}_p(s,\phi) = \sum_{l=-\infty}^{+\infty} c_l(s) e^{il\phi} \qquad (17)$$

vanish for $|l| \geq M$.

This example illustrates two important points. First, to achieve perfect reconstruction it is generally necessary to augment the basic assumptions (7) about the target function F. Second, perfect reconstruction may require a "global" G-function, i.e. one that couples each cartesian frequency to every polar frequency. The result, as pointed out by R. N. Bracewell (1979, "Image Reconstruction in Radio Astronomy", in Image Reconstruction from Projections: Implementation and Applications, G. T. Herman, Ed. (Berlin: Springer), pp. 81–104) is an algorithm that is less efficient than filtered backprojection. Previous studies of the DFI method have therefore concentrated on "local" interpolation schemes, with the result that image quality is sacrificed to some degree in return for computational efficiency. (See the papers by Low, K.-H., and F. Natterer, 1981, "An Ultra-Fast Algorithm in Tomography", Tech. Rept. A81/03, Fachbereich Angewandte Mathematik und Informatik, U. des Saarlandes, 6600 Saarbrucken, West Germany, R. M. Mersereau, 1976, "Direct Fourier Transform Techniques in 3D Image Reconstruction", Comput. Med. Biol., vol. 247–258, Mersereau, R. M., and A. V. Oppenheim, 1974, "Digital Reconstruction of Multi-Dimensional Signals from their Projections", Proc. IEEE, vol. 62, pp. 1319–1338, Niki, N., T. Mizutani, Y. Takahashi, and T. Inouye, 1983, "High-Speed Computerized Tomography Image Reconstruction Using Direct Two-Dimensional Fourier Transform Method", Systems.Computers.Controls, vol. 14, pp. 56–65, and Stark, H., J. W. Woods, I. Paul, and R. Hingorani, 1981, "An Investigation of Computed Tomography by Direct Fourier Inversion and Optimum Interpolation", IEE Transactions on Acoustics, {Speech, and Signal Processing, vol. ASSP-29, pp. 237–245). The yet-to-be-obtained goal is to find a compromise that produces image quality comparable to that of filtered backprojection.

A technique frequently employed in various forms of signal processing is the multiplication of the signal's transform by a low-pass filter. As a final as4de, we note that such filters can be incorporated in the DFI method by a suitable definition of G. Thus the algorithm $$G(s_{\gamma\lambda}|s_{\sigma\mu}) = G_3(S_{\gamma\lambda}) G_2(s_{\gamma\lambda}|S_{\sigma\mu})G_1(s_{\sigma\mu}) \quad (18)$$

multiplies $\hat{F}_P(s_{\sigma\mu})$ by the "polar filter" $G_1$, interpolates with function $G_2$ to find $F_c(s_{\gamma\lambda})$, and multiplies the result by the "cartesian filter" $G_3$.

(b) Operations Count

The steps described above allow us to write down the operations count for a DFI algorithm in terms of G. Note that, since F is real-valued, its transform is hermitian. Thus one only needs to compute $F_p$ and $F_c$ on the upper half-plane in frequency space (See FIG. 5). The operations are:

(1) Use (8) to find $\hat{F}_p(s_{\sigma\mu})$ for $0 \leq \mu \leq M$ and $0 \leq \sigma < N/2$ using an FFT routine, followed by a post-multiplication to shift the frequency origin. This requires $n_1 = MN (2\log_2 N + 2)$ operations.

(2) Interpolate to obtain $\hat{F}_c$ at $\frac{1}{2} K^2$ cartesian frequencies in the upper half-plane. Assume that G couples each cartesian frequency to L polar frequencies and that it takes J operations to evaluate G once. Then the cost of this step is $n_2 = \frac{1}{2} K^2 L J$ operations.

(3) Evaluate (11) using a two-dimensional, inverse FFT routine, preceded by a multiplication to shift the frequency origin. This takes $n_3 = K^2(4\log_2 K + 2)$ operations.

Adding $n_1$, $n_2$, and $n_3$ gives Property 1: A DFI algorithm with interpolation function G requires operations.

$$n = K^2 \left( \frac{MN}{K^2} (2\log_2 N + 2) + 4\log_2 K + \frac{1}{2}LJ + 2 \right) \quad (19)$$

An analysis of sampling in angle (See Mersereau, R. M., and A. V. Oppenheim, 1984, "Digital Reconstruction of Multi-Dimensional Signals from their Projections", Proc. IEEE, vol. 62, pp. 1319–1338 and Stark, H., J. W. Woods, I. Paul, and R. Hingorani, 1981, "An Investigation of Computed Tomography by Direct Fourier Inversion and Optimum Interpolation", IEE Transactions on Acoustics, Speech, and Signal Processing, vol. ASSP-29, pp. 237–245) shows that the angular sampling increments must be such that $M \geq \pi/2N$ and, if if $\Delta x \geq \Delta t$, then (13) implies $K \geq N$. Taking $M \approx N$ and $K \approx N$, and assuming that $J = O(1)$ (if necessary, by using a table look-up to evaluate G) we have Property 2: The operations count scales as $n \propto K^2$ provided $L << K$. This is just the requirement that G be local.

(c) Explicit Signal-Space Reconstruction Formula

By a signal-space reconstruction method, such as filtered backprojection, we mean an algorithm of the form $$\overline{F}(x_{\alpha\beta}) = \sum_\tau \sum_\mu W(x_{\alpha\beta}|t_{\tau\mu})P(t_{\tau\mu}), \quad (20)$$

where W is a known function of the arguments $t_{\tau\mu}$ and $x_{\alpha\beta}$. We refer to such an algorithm by its W-function. Now (8), (14), and (11) may be combined to yield $$\overline{F}(x_{\alpha\beta}) = \frac{\Delta t}{(K\Delta x)^2} \sum_\gamma \sum_\lambda \sum_\sigma \sum_\mu \sum_\tau e^{2\pi i(\frac{\alpha\gamma}{K} + \frac{\beta\lambda}{K} - \frac{\sigma\tau}{N})} G(s_{\gamma\lambda}/s_{\sigma\mu})P(t_{\tau\mu}), \quad (21)$$

a result summarized in Property 3: A DFI algorithm G is equivalent to the signal-space algorithm $$W(x_{\alpha\beta}|t_{\tau\mu}) = \quad (22)$$

$$\frac{\Delta t}{(K\Delta x)^2} \sum_\gamma \sum_\lambda \sum_\sigma e^{2\pi i(\frac{\alpha\gamma}{K} + \frac{\beta\lambda}{K} - \frac{\sigma\tau}{N})} G(s_{\gamma\lambda}/s_{\sigma\mu})$$

in the sense that the algorithms give identical values of $\overline{F}(x_{\alpha\beta})$ on the grid $x_{\alpha\beta}$.

(d) Point-Spread Function

If assumption (7) is valid, then (14) is an exact relation between the interpolated and true transforms of F at certain discrete frequencies. Suppose, however, that the interpolation scheme had been used to construct $\hat{F}(s)$ everywhere in frequency space via $$\overline{F}(s) = \sum_\sigma \sum_\mu G(s|s_{\sigma\mu}) \hat{F}_P(s_{\sigma\mu}), \quad (23)$$

for $-\infty < s_1, s_2 < +\infty$ and not just at points in the cartesian grid. Then we could obtain a reconstruction by taking the continuous inverse transform, $$F(x) = \int ds \, \overline{F}(s) \, e^{+2\pi i x s} \quad (24)$$

By writing $\hat{F}_p(s_{\sigma\mu})$ in terms of F via (4), we can combine (23) and (24) to give:

$$\overline{F}(x) = \int dx' \, H(x|x') \, F(x'), \quad (25a)$$

where $$H(x|x') = \sum_\sigma \sum_\mu e^{-2\pi i x' s_{\sigma\mu}} \int ds \, G(s|s_{\sigma\mu}) \, e^{+2\pi i x s} \quad (25b)$$

Henceforth, we shall refer to H as the point-spread function, although the common definition of this term is more restrictive.

Now (25) is also valid in the practical case of discrete interpolation provided (1) the interpolated transform $\hat{F}_c$ vanishes outside the cartesian frequency raster and (2) $F_c$ is Nyquist-sampled by the cartesian frequency grid. Condition (1) can always be satisfied by filtering $\hat{F}_c$. Condition (2) is the same as (13), which is satisfied if $N\Delta t > 2R$, i.e. if the target falls to zero inside the region sampled by the scans.

Gathering together these ideas, we have Property 4: A DFI reconstruction $\overline{F}$ and target F are related by (25) provided that (1) assumptions (7) are valid, (2)

$N\Delta t > 2R$, and (3) the interpolation scheme makes $\widetilde{F}_c$ vanish outside the cartesian frequency grid.

The integrals in (25b) simplify for a special case of some interest. This is Property 5: Suppose that $G(s\ s')$ depends on s and s' only through s−s': $G(s\ s')=G(s-s')$. If the hypotheses of Property 4 are satisfied, then the target and reconstruction are related by $$\widetilde{F}(x) = \hat{G}(s) \int dx'\ H(x - x')\ F(x'), \quad (26a)$$

where $$H(x - x') = \sum_\sigma \sum_\mu e^{+2\pi i(x-x')s\sigma\mu}. \quad (26b)$$

We see that the term point-spread function is appropriate for this special case.

Notice that G enters (26a) only as the multiplicative distortion factor $\hat{G}(x)$. If we choose a G-function whose transform has no zeroes inside the domain T, then we can remove the distortion by a postmultiplication. Alternatively, we can choose a G-function whose distortion factor is close to unity everywhere in the image. Notice also that the kernel H(x-x') in the convolution integral is determined once and for all by the frequencies in the polar raster. And finally, the Fourier transform of H is a set of delta functions centered at each frequency $s_{\sigma\mu}$; thus it is impossible to perform a deconvolution on (26a).

(e) The Noise Amplification Factor

At each point, the target and reconstruction will differ for a variety of reasons. In the preceding section, we discussed systematic errors caused by approximations in the reconstruction scheme. These depend on the particular properties of each target and reconstruction algorithm, but are inherent in any method that uses discrete projection data. Here we consider random errors, which are introduced by statistical fluctuations in the measured projections, and propagated by the algorithm. Consider the projection $P(t_{\tau\mu})$ for a particular value of $t_{\tau\mu}$. An estimate of $P(t_{\tau\mu})$ is obtained by directing a pencil beam of radiation along the appropriate ray, and measuring the numbers $N_I$ and $N_T$ of photons that enter and leave the target. According to Beer's Law, the projection is given by $$\widetilde{P}(t_{\tau\mu}) = \ln \widetilde{N}_I/\widetilde{N}_T, \quad (27)$$

where the tildes emphasize the distinction between exact and measured quantities. We shall adopt the standard assumptions, justified elsewhere, that $\widetilde{N}_I$ and $\widetilde{N}_T$ obey Poisson statistics and that $\widetilde{N}_I >> \widetilde{N}_T >> 1$. Then from (20) it follows that the mean error in $\widetilde{P}(t_{\tau\mu})$ is zero, and the standard deviation is $$\sigma_P^2(t_{\tau\mu}) = 1/\widetilde{N}_T \quad (28)$$

(See R. A. Brooks and G. Di Chiro, 1976, "Statistical Limitations in X-Ray Reconstructive Tomography", Medical Physics, vol. 3, pp. 237–240, and Chesler, D. A., S. J. Riederer, and N. J. Pelc, 1977, "Noise Due to Photon Counting Statistics in Computed X-Ray Tomography", Journal of Computer Assisted Tomography, vol. 1, pp. 64–74). Notice that these statistics refer to a sequence of identical trial measurement of $\widetilde{P}(t_{\tau\mu})$, with the argument $t_{\tau\mu}$ fixed. Also note that, since $\widetilde{N}_T$ depends on $P(t_{\tau\mu})$, the errors will be correlated unless all the projections are identical. That is, $\tau_P{}^2(t_{\tau\mu})$ generally depends on $t_{\tau\mu}$.

The linearity of (20) in $P(t_{\tau\mu})$ implies a simple relationship between random errors in $\widetilde{F}(x_{\alpha\beta})$ and $\widetilde{P}(t_{\tau\mu})$. Let $\sigma_f^2(x_{\alpha\beta})$ be the variance in $\widetilde{F}(x_{\alpha\beta})$ at a particular point $x_{\alpha\beta}$. A consequence of (20) and the theory of statistics is that the mean error in $\widetilde{F}(x_{\alpha\beta})$ is zero, and that $$\sigma_f^2(x_{\alpha\beta}) = \sum_\tau \sum_\mu W(x_{\alpha\beta}\ t_{\tau\mu})^2 \sigma_P^2(t_{\tau\mu}). \quad (29)$$

[cf. R. W. Hamming, 1983, Digital Filters, (Englewood Cliffs, N.J.: Prentice-Hall]. The substitution of (22) into (29) gives the variance $\sigma_f^2(x_{\alpha\beta})$ in terms of the G-function. This is our basic result. Equations (22) and (29) are exact expressions, provided only that our statistical assumptions above about $\widetilde{N}_I$ and $\widetilde{N}_T$ are valid. Again, we stress that the mean and variance refer to averages over a sequence of measurements with $x_{\alpha\beta}$ fixed. Note that errors in $\widetilde{F}(x_{\alpha\beta})$ may be correlated with one another, even when errors in the projections are not.

While (29) gives a complete description of noise amplification by DFI methods, it is seldom practical to evaluate this expression for all $K^2$ points in an image. A more useful result is obtained by considering the limit where all of the projections are identical, i.e. $P(t_{\tau\mu}) = P$ independent of $t_{\tau\mu}$. Then according to (27) and (28), $\sigma_P^2(t_{\tau\mu})$ is also a constant, $\sigma_P^2$, so that errors in P are uncorrelated. Bringing $\sigma_P^2$ outside the sum in (29), and substituting expression (22) for $W(x_{\alpha\beta}t_{\tau\mu})$, we find $$\sigma_f^2(x_{\alpha\beta}) = \sigma_P^2 \frac{\Delta t^2}{K^4 \Delta x^4} \sum_\tau \sum_\mu \sum_\gamma \sum_{\gamma'} \sum_\lambda \sum_{\lambda'} \sum_\sigma \sum_{\sigma'} e^{2\pi i [\frac{\alpha(\gamma-\gamma')}{K} + \frac{\beta(\lambda-\lambda')}{K} - \frac{\tau(\sigma-\sigma')}{N}]} \times G(s_{\gamma\lambda}|s_{\sigma\mu}) G^*(s_{\gamma\lambda'}|s_{\sigma\mu}). \quad (30)$$

where the asterisk denotes complex conjugation.

To proceed, consider the variance averaged over the image, $$\overline{\sigma_f^2} = \frac{1}{K^2} \sum_\alpha \sum_\beta \sigma_f^2(x_{\alpha\beta}) \quad (31)$$

According to (30), this is $$\overline{\sigma_f^2} = \sigma_P^2 \frac{\Delta t^2}{K^6 \Delta x^4} \sum_\gamma \sum_\lambda \sum_\sigma \sum_\mu G\left(s_{\gamma\lambda}|s_{\sigma\mu}\right) \sum_{\gamma'} \sum_{\lambda'} \sum_{\sigma'} G^*(s_{\gamma'\lambda'}|s_{\sigma'\mu}) \times \sum_\alpha e^{\frac{2\pi i}{K}\alpha(\gamma-\gamma')} \sum_\beta e^{\frac{2\pi i}{K}\beta(\lambda-\lambda')} \sum_\tau e^{\frac{-2\pi i}{N}\tau(\sigma-\sigma')} \quad (32)$$

The sums over $\alpha$, $\beta$ and $\tau$ can be evaluated by inspection using the identity $$\frac{1}{J} \sum_{\nu=-J/2}^{J/2-1} e^{\frac{2\pi i}{J}\nu(p-p')} = \delta_{p,p'} \quad (33)$$

where J, p, p' are integers. The simplified result is $$\overline{\sigma_f^2} = \sigma_P^2 \frac{N\Delta t^2}{K^4 \Delta x^4} \sum_\gamma \sum_\lambda \sum_\sigma \sum_\mu G(s_{\gamma\lambda}|s_{\sigma\mu})^2. \quad (34)$$

It is convenient to rewrite (34) as a relation between two dimensionless quantities. This is accomplished by introducing the reconstruction averaged over the image, $$\overline{\overline{F}} = \frac{1}{K^2} \sum_\alpha \sum_\beta \overline{F(x_{\alpha\beta})}. \quad (35)$$

We can use (20) and (22) to express this as $$\overline{\overline{F}} = \quad (36)$$

$$\frac{P\Delta t}{K^4 \Delta x^2} \sum_\gamma \sum_\lambda \sum_\sigma \sum_\mu G(s_{\gamma\lambda}|s_{\sigma\mu}) \sum_\alpha e^{\frac{2\pi i}{K} \alpha\gamma} \sum_\beta e^{\frac{2\pi i}{K} \beta\lambda} \sum_\tau e^{\frac{-2\pi i}{N} \sigma\tau}.$$

Once again, (33) is used to evaluate the innermost sums, giving $$\overline{\overline{F}} = \frac{NP\Delta t}{K^2 \Delta x^2} \sum_\mu G(s_{00}|s_{0\mu}). \quad (37)$$

Now in practice the sum over $\mu$ in (37) is always unity, which can be seen as follows. The frequencies $s_{00}$ and $s_{0\mu}$ are all identically zero according to (9) and (10). Hence the expression involving $\mu$ is just the sum of the weights in the interpolation for the transform at the origin. If we require that the reconstruction be properly normalized, the sum must equal unity. Therefore $$\overline{\overline{F}} = \frac{NP\Delta t}{K^2 \Delta x^2} \quad (38)$$

If we also recall that the scan diameter, $N\Delta t$, equals the sidelength of the image, $K\Delta x$, then we see from (38) that $P = \overline{\overline{F}} \times K\Delta x$, as it should be.

Finally, if we divide both sides of (34) by the square of (38), the former can be recast as $$[\overline{\sigma_f^2}/\overline{\overline{F}}^2]^{\frac{1}{2}} = [\sigma_P/P]\omega \quad (39)$$

where $$\omega = \frac{K}{\sqrt{N}} \left( \frac{1}{K^2} \sum_\gamma \sum_\lambda \sum_\sigma \sum_\mu G(s_{\gamma\lambda}|s_{\sigma\mu})^2 \right)^{\frac{1}{2}} \quad (40)$$

In the limit where there are no correlations amongst the measurement errors, the noise-to-signal ratio in the image equals the noise-to-signal ratio in the projections times the "amplification factor" $\omega$. Given any DFI algorithm, (40) can be used to find $\omega$ in terms of G.

(f) Application

As an application of our analysis, we study one of the simplest DFI algorithms, an L=4 scheme which is known to produce images of poor quality (See Mersereau, R. M., and A. V. Oppenheim, 1974, "Digital Reconstruction of Multi-Dimensional Signals from their Projections", Proc. IEEE, vol. 62, pp. 1419–1338). In part (i) below we use the foregoing analysis to identify some of its defects. In part (ii) we suggest some minor changes that lead to dramatic improvements in the reconstructions.

(i) Reconstructions Using the Basic DFI Method
Consider the algorithm $$G(ss') = \Lambda\left[\frac{s - s'}{\Delta s}\right] \Lambda\left[\frac{\phi - \phi'}{\Delta \phi}\right] \quad (41)$$

where $\Lambda$ is the triangle function $$\Lambda(x) \equiv \begin{cases} 1 - |x| & \text{if } |x| < 1 \\ 0 & \text{if } |x| > 1 \end{cases} \quad (42)$$

This scheme finds $\overline{F}_c(s_{\gamma\lambda})$ by linear interpolation in the polar coordinates $s$ and $\phi$, the interpolants being the L=4 points that form a "tile" surrounding $s_{\gamma\lambda}$ (see FIG. 9).

FIG. 10 is a target ("TARGET") and its reconstruction ("DFI") obtained with algorithm (41). The function in FIG. 10 is defined to be constant on each of 256×256 square pixels. Its projections were calculated at N=256 and M=400 equally-spaced impact parameters and angles, respectively, using a computer program developed for that purpose. The program emulates an ideal CT scanner with uniform beam profile and detector response functions, both one pixel wide; the ray spacing $\Delta t$ was taken to be 1.5 times the pixel width. For comparison, we also give in FIG. 10 a reconstruction ("FBP") obtained from the same scan data, using a filtered backprojection program given by Shepp and Logan (1974, "The Fourier Reconstruction of a Head Section", IEEE Trans. Nucl. Sci., vol. NS-21, pp. 21–43). We have used the filter function they call $\overline{\phi}$.

According to Property 2, the operations count for this algorithm should be proportional to $K^2$, a prediction we have tested empirically. Scans of the target were generated for a range of parameters N and M and both DFI and FBP reconstructions were obtained for several K values, using a Floating Point Systems 164 array processor. The DFI program was written to implement algorithm (41) and the FBP program was that of Shepp and Logan, optimized to make full use of the FPS-164's vector-processing capabilities. In FIG. 4 we plot the logarithm of the CPU time required to reconstruct one slice versus $\log_{10} N$. The x's are the results for FBP with "standard" parameters M=100 (N/64) and K=N. The other symbols refer to the DFI method; the three different symbol types represent the cases K=N, K=N/2, and K=N/4.

Not surprisingly, the x's define a straight line with slope 3 and each of the other symbol types defines a line with slope 2. The reason for plotting FIG. 4 is to show that the DFI algorithm is an order of magnitude faster than FBP, even for the smallest image, N=64. For a 512×512 image, the DFI algorithm takes about 5 seconds versus more than ten minutes for FBP on this particular computer.

Next we consider some of the defects of algorithm (41), starting with artifacts in the reconstruction. These are minimal in FIG. 10 because the target contains only a few large, Gaussian features Its Fourier transform is peaked at the origin, where the polar grid is densest and, accordingly, the interpolation is good. However, consider the target depicted in FIG. 11 and its reconstructions by DFI and FBP. The target function is defined to be unity inside a square and zero outside. Notice that the DFI reconstruction contains large-amplitude, low-frequency distortion which is most pronounced outside the square and small-amplitude, high-frequency oscillations concentrated inside.

Some insight into these problems is provided by Property 4. First note that the non-zero region of F nearly fills the image so that hypothesis (2) of Property 4 is satisfied only marginally. Consequently $F_p(s, \phi)$ is nearly undersampled by the polar grid, with the result that aliasing occurs in the reconstruction. This effect has been noted elsewhere. (See the papers by Lewitt, R. M., 1983, "Reconstruction Algorithms: Transform Methods", Proc. IEEE, vol 71, pp. 390–408, and Low, K-H., and F. Natterer, 1981, "An Ultra-Fast Algorithm in Tomography", Tech. Rept. A81/03, Fachbereich Angewandte Mathematik und Informatik, U. des Saarlandes, 6600 Saarbrucken, West Germany).

According to (25b), the point-spread function for this algorithm is $$H(x|x') = \sum_\sigma \sum_\mu J_{\sigma\mu}(x) e^{-2\pi i x' s \sigma \mu}, \quad (43a)$$

where $$J_{\sigma\mu}(x) = \int_{-\infty}^{+\infty} ds|s| \int_{-\infty}^{+\infty} d\phi \Lambda \frac{s - s_\sigma}{\Delta s} \Lambda \frac{\phi - \phi_\mu}{\Delta \phi} e^{+2\pi i x s} \quad (43b)$$

In FIG. 12 we give a perspective plot of H as a function of $x'$ with x fixed at the origin. The apparent circular symmetry of the figure reflects our choice of the special point $x = 0$, and is not a general property of H.

Notice that H has prominent sidelobes and recall that Gibbs phenomenon arises when a discontinuous function is convolved with another function that possesses such lobes. We attribute the small-scale distortion in the DFI reconstruction to Gibbs phenomenon, caused by our implicit choice of H for this algorithm. To see this more clearly, consider FIG. 13, which is a plot of H along part of the $x'_1$-axis It shows that the sidelobes oscillate at the Nyquist frequency, $\frac{1}{2}\Delta t$, and that their amplitude falls off rather slowly with $x'_1$. The implication is that image will contain oscillations at this frequency, which persist far from sharp edges This is consistent with the artifacts in the image.

The last step in our analysis of algorithm (41) is to find its noise amplification factor At each point $s_{\gamma\lambda}$, the interpolation weights in (40) depend on the position of $s_{\gamma\lambda}$ relative to the four corners of the tile in FIG. 9. It seems reasonable to assume that, for the set $s_{\gamma\lambda}$ as a whole, the distribution of these positions is uniform in radius and angle. Then it is straightforward to show that, in 40), the expression in curly brackets is just $\frac{2}{3}$, giving $\omega \approx 2K/3\overline{N}$. This assumes that all cartesian frequencies contribute to (40). However when $K \geq N$, some of the $s_{\gamma\lambda}$ fall outside the circle $s = \frac{1}{2}\Delta t$ where, by hypothesis (7), the transform is zero. In our computer codes, we set $F_c(s_{\gamma\lambda})$ to zero explicitly in this region so that (40) should only include points inside the circle. The result is to modify our formula for $\omega$ somewhat, giving, $$\omega = \begin{cases} \frac{2K}{3\sqrt{N}} & \text{if } K < N \\ \frac{1}{3}\sqrt{N\pi} & \text{if } K \geq N \end{cases} \quad (44)$$

The predictions of (44) were tested by numerical experiments which simulated the effect of random noise in the scans. In each of a sequence of identical trials, a scan of M angles and N impact parameters was created by setting $$\overline{P(t_{\tau\mu})} = \overline{P} + \sigma_p \eta(t_{\tau\mu}), \quad (45)$$

where $\overline{P}$ and $\sigma_p$, are constants, and $\eta(t_{\tau\mu})$ is a standard normal random variable, sampled independently on each trial and at each $t_{\tau\mu}$. After the n-th trial in the sequence, a reconstruction was performed on the scan data, and at each $x_{\alpha\beta}$ the averages $<\overline{F^2}(x_{\alpha\beta})>$ and $<\overline{F^2}(x_{60\beta})>$ over trials one through n were calculated. Then from the variance at each $x_{\alpha\beta}$.

$$\sigma_f^2(x_{60\beta}) = <\overline{F^2}(x_{\alpha\beta})> - <\overline{F}(x_{\alpha\beta})>^2, \quad (46)$$

we evaluated the "observed" amplification factor $$\varphi = \frac{[\overline{\sigma_f^2/F^2}]^{\frac{1}{2}}}{[\sigma_P/\overline{P}]} \quad (47)$$

When $\overline{\omega}$ converged to three significant figures, the sequence was terminated. For each N, we set $M = 100(N/64)$ and conducted independent experiments for the cases $K = N$, $N/2$, $N/4$, and $N/8$.

The results of these trials are plotted in FIG. 14. The four solid curves are plots of expression (44) for the different cases K(N); the four symbol types apply to the corresponding experiments. The agreement between theory and experiment is within the precision to which $\overline{\omega}$ was calculated, although the experimental values are systematically smaller than the theoretical predictions This probably reflects the error associated with our assumption, that the cartesian frequencies are uniformly distributed in polar coordinates. FIG. 14 emphasizes the fact that algorithm (41) amplifies noise. For reconstruction at comparable resolution, the $\omega$ factor for Shepp and Logan's FBP algorithm is considerably smaller by comparison. When $N = 256$ $\omega$ is 5.4 for FBP with their filter function $\phi$, which corresponds roughly to the case $K = N$. For their filter function $\overline{\phi}$, which corresponds to somewhat higher resolution than $K = N/2$, it is 2.2. (The $\omega$ values are independent of K for FBP).

(ii) Reconstructions Using Our Improved DFI Method

The preceding results suggest a rational procedure for improving algorithm (41). Our main objective is to improve image quality, which basically amounts to suppressing the sidelobes on the pointspread function H. The important point is that, having explicit expressions for H via Properties 4 and 5, we are able to bring the large body of knowledge on digital filtering to bear on the problem.

Aliasing caused by undersampling in the polar grid is a well-studied defect of DFI methods See, for example, Lewitt, R. M., 1983, "Reconstruction Algorithms: Transform Methods", Proc. IEEE, vol. 71, pp. 390–408, Low, K.-H., and F. Natterer, 1981, "An Ultra-Fast Algorithm in Tomography", Tech Rept A81/03, Fachbereich Angewandte Mathematik und Informatik, U. des Saarlandes, 6600 Saarbrucken, West Germany, and Stark, H., J. W. Woods, I. Paul, and R. Hingorani, 1981, "An Investigation of Computed Tomography by Direct Fourier Inversion and Optimum Interpolation", IEE Transactions on Acoustics, Speech, and Signal Processing, vol. ASSP-29, pp. 237-245). The remedy for undersampling in the radial direction is simple: one uses the standard sinc interpolation for a uniformly sampled function However since interpolation is non-local, making $L=N$ and the operations count scale as $n \propto K^3$ (Property 1). To reduce L to order unity, one can replace sinc with $f(s-s_\sigma)$ sinc $(s-\sigma)$, where f is a monotonic decreasing function, chosen to make the Fourier transform of $f(s)$sinc$(s)$ as close as possible to a rectangular window Here we use another simple remedy, suggested in the paper by Lewitt and also by Niki, N., T. Mizutani, Y. Takahashi, and T. Inouye, 1983, "High-Speed Computerized Tomography Image Reconstruction Using Direct Two-Dimensional Fourier Transform Method", Systems.- Computers.Controls, vol. 14, pp. 56-65. For each value of $\mu$, we pad $P(t_{\tau\mu})$ with zeroes in the $t_1$-direction before evaluating (8), simulating the effect of scanning some "empty space" around the target Since the radial spacing in the polar grid is $\Delta s = 1/N\Delta t$, padding by a factor Q decreases $\Delta s$ by $1/Q$. This effectively changes N to QN in expression (19) for the operations count, which increases the cost per reconstruction somewhat. However if Q is of order unity, we see that the scaling law, $n \propto K^2$, still holds.

The effect of padding is illustrated in FIG. 15, where we plot $\hat{p}(\sigma,\mu)$ versus $\sigma$, with $\mu=1$. The scan data $P(t_{\tau\mu})$ used to compute $\hat{p}(\sigma,\mu)$ were obtained from the target in FIG. 10, using the scanning program described above The open circles in FIG. 15 are the real part of $\hat{p}$ computed with no padding; the imaginary part is zero for this particular target. The solid circles are $\hat{p}$ computed with padding by a factor $Q=4$. At integral values of $\sigma$ the points coincide; in each intervening interval the transform with padding is calculated at 3 additional points. It is hardly surprising that linear interpolation in the solid circles produces better images This is confirmed in the image labelled "DFI+PAD" in FIG. 11, which was obtained with algorithm (41) plus padding by $Q=8$.

In many cases, padding even by $Q=2$ is sufficient to guarantee a satisfactory reconstruction. No amount of padding suffices in medical applications, however, because padding does not eliminate the overshoot effect, which obliterates low contrast features of interest. This point is illustrated in FIGS. 6 and 7. FIG. 6 is the simulated medical target devised by Shepp and Logan (1974, "The Fourier Reconstruction of a Head Section", IEEE Trans. Nucl. Sci., vol. NS-21, pp. 21-43). It resembles a head section, in which the function F rises sharply from zero outside the head, to $F=2$ in the skull, and then quickly back to $F \approx 1$ in the interior. Function values in the interior range from 0.99 to 1.04, including three small features meant to represent tumors. FIG. 7 shows reconstructions of the medical target with algorithm (41) ("DFI") and with the same algorithm plus padding by $Q=8$ ("DFI+PAD"). Although padding improves the reconstruction somewhat, it does not eliminate the high frequency oscillations that completely obscure features close to the skull. Perhaps this is why DFI methods are not in common use.

The standard method for removing overshoot is to multiply the transform by a low-pass filter. That this is the correct strategy is suggested also by expression (26b). The latter shows that, for one class of algorithms at least, H is determined solely by the points in the polar grid. Thus it is futile to try, for example, to improve the reconstruction by modifying the functional dependence of G. Keeping this in mind, we have tried a few algorithms of the form (18), where $G_2$ corresponds to algorithm (41) with padding by $Q=8$ included, and $G_1$ and $G_3$ are low-pass filters (FIG. 7 also illustrates the results of simply adding FILTERING to the DFI algorithm, without PADDING. Obviously, filtering alone does little to improve image quality). The panel in FIG. 7 labelled "DFI+PAD+FILTER" is a reconstruction of the head section with the Hanning function, $$G_1(s_{\sigma\mu}) = \frac{1}{2}[1 + \cos(\pi s_\sigma/s^*)], \tag{48}$$

used for the polar filter, $G_1$, and the Lanczos function, $$G_3(s_{\gamma\lambda}) = \frac{\sin(\pi s_{1,\gamma}/s^*)}{(\pi s_{1,\gamma}/s^*)} \frac{\sin(\pi s_{2,\lambda}/s^*)}{(\pi s_{2,\lambda}/s^*)}. \tag{49}$$

used for the cartesian filter, $G_3$. The cutoff frequency, $s^*$, is a parameter that determines the degree to which filtering degrades the resolution. We have arbitrarily chosen the cutoff frequency to be $s^*=0.5/\Delta t$, i.e. the Nyquist frequency.

The combination of improved interpolation through PADDING and FILTERING to remove high frequency oscillations together of produce images quality comparable to FBP, but in much less processing time.

The panel in FIG. 8 labelled "FBP" is the reconstruction obtained with filtered backprojection, using Shepp and Logan's filter function $\overline{\phi}$. A comparison of the images shows that, by adding Filtering and PADDING, one can obtain DFI images that compare in quality to filtered backprojection.

The comparisons are made quantitative in FIGS. 16-19 which show the variation of density, in arbitrary absolute units, along a short cross section through the region of the image plane containing three small features meant to represent low contrast tumors in the simulated target. FIGS. 16 shows the original target, or phantom, from which the simulated data were obtained. FIG. 17 shows a reconstruction using FBP. The tumors are distinctly present but the density variation shows some noise introduced by the scanning and reconstruction procedures FIG. 18 shows a reconstruction using DFI+PAD, but without filtering. While the visual image begins to resemble the target, noise and artifacts are present at an amplitude that obscures the image FIGS. 19 shows an image obtained using the methods disclosed here that include DFI+PAD+FILTER. The image and the density variation along the cross section show results that are comparable to results obtained using FBP, but that require far less processing time. In fact the noise level in FIG. 19 along the cross section is somewhat lower than with FBP.

Finally, we note that our improved DFI method has acceptable efficiency and noise amplification factor. Filtering adds virtually nothing to the operations count of algorithm (41), but padding by $Q=8$ increases the time to reconstruct a $256 \times 256$ image from 1.5 sec to about 3.9 sec. For the same parameters, filtered backprojection takes about 86 sec. And last, filtering has the desirable side-effect that it reduces $\omega$ from 9.5 for algorithm (41) to 2.7 for the improved DFI algorithm.

What is claimed is:

1. A method for examining at least a portion of an object using penetrating radiation directed from a variety of view angles about a rotation axis through the object comprising:
   (a) transmitting incident radiation from an external source through portions of the object having sharp density variations in a plurality of coplanar rays so that said radiation is attenuated as it passes through said object,
   (b) detecting said attenuated transmitted radiation after it has passed through the object,
   (c) determining the projection data from said attenuated transmitted radiation and said incident radiation for said rays, and
   (d) inverting said projection data to generate the distribution of the attenuation coefficients wherein said inverting step includes the Direct Fourier Inversion Method such that the projection data are padded and the Fourier coefficients are filtered, wherein said Direct Fourier Inversion Method can generate said distribution of attenuation coefficients, for an object having sharp density variation such as in a Shepp-Logan target.

2. The method of claim 1 wherein said radiation is transmitted from said external source in the parallel beam observational mode.

3. The method of claim 2 wherein said step of inverting said project data includes the steps of
   (a) taking a fast Fourier transform of said projection data at a given angle, after first padding the data to determine the Fourier coefficients on a polar raster,
   (b) shifting the phase of said Fourier coefficients to said rotation axis (target origin), and applying a low pass filter,
   (c) repeating steps (a) and (b) for the projection data at each view angle,
   (d) interpolating said Fourier coefficients from a polar raster to a Cartesian grid,
   (e) shifting the phase to the Cartesian origin, and applying a low pass filter
   (f) taking an inverse fast Fourier transform producing the image of the object.

4. The method of claim 3 wherein the interpolating step is a linear interpolation from polar to Cartesian coordinates, the interpolants being the 4 points in the polar tile surrounds the desired Cartesian point (as illustrated in FIG. 9).

5. The method of claim 3 wherein said filter is a low pass filter.

6. The method of claim 3 wherein said filter is a Hanning function in polar coordinates times a Lanczos function in Cartesian coordinates.

7. The method of claim 1 wherein said radiation is x-radiation.